(12) United States Patent
Nakafuji et al.

(10) Patent No.: US 9,620,378 B1
(45) Date of Patent: Apr. 11, 2017

(54) COMPOSITION FOR FILM FORMATION, FILM, PRODUCTION METHOD OF PATTERNED SUBSTRATE, AND COMPOUND

(71) Applicant: JSR Corporation, Tokyo (JP)

(72) Inventors: Shin-ya Nakafuji, Tokyo (JP); Goji Wakamatsu, Tokyo (JP); Tsubasa Abe, Tokyo (JP); Kazunori Sakai, Tokyo (JP)

(73) Assignee: JSR CORPORATION, Tokyo (JP)

( * ) Notice: Subject to any disclaimer, the term of this patent is extended or adjusted under 35 U.S.C. 154(b) by 0 days.

(21) Appl. No.: 14/757,551

(22) Filed: Dec. 24, 2015

(51) Int. Cl.
| | |
|---|---|
| G03F 7/11 | (2006.01) |
| H01L 21/308 | (2006.01) |
| H01L 21/027 | (2006.01) |
| C09D 7/12 | (2006.01) |
| C09D 201/00 | (2006.01) |
| C09D 171/08 | (2006.01) |
| C07C 255/54 | (2006.01) |
| C09D 171/12 | (2006.01) |

(52) U.S. Cl.
CPC ........ *H01L 21/3081* (2013.01); *C07C 255/54* (2013.01); *C09D 171/12* (2013.01); *C09D 201/00* (2013.01); *G03F 7/11* (2013.01); *H01L 21/0273* (2013.01); *H01L 21/3086* (2013.01); *C07C 2103/18* (2013.01)

(58) Field of Classification Search
None
See application file for complete search history.

(56) References Cited

U.S. PATENT DOCUMENTS

| | | | | |
|---|---|---|---|---|
| 6,468,589 B2 * | 10/2002 | Nishikawa et al. | ... | C08G 65/40 427/385.5 |
| 2002/0086968 A1 * | 7/2002 | Haussmann et al. | .. | C08G 73/22 528/128 |
| 2004/0002572 A1 * | 1/2004 | Enoki et al. | ........... | C08G 69/48 524/606 |
| 2004/0127632 A1 * | 7/2004 | Kim et al. | ............ | C07C 43/225 524/544 |
| 2006/0234158 A1 * | 10/2006 | Hatakeyama | ........... | G03F 7/094 430/270.1 |
| 2010/0003447 A1 * | 1/2010 | Suzuki et al. | ..... | G11B 7/00452 428/65.1 |
| 2010/0099044 A1 * | 4/2010 | Hatakeyama et al. | .. | G03F 7/095 430/285.1 |
| 2014/0272722 A1 * | 9/2014 | Nakafuji et al. | .......... | G03F 7/11 430/323 |
| 2016/0046551 A1 * | 2/2016 | Shiota et al. | ........... | C07C 69/54 558/46 |

FOREIGN PATENT DOCUMENTS

| | | | |
|---|---|---|---|
| CN | 101503488 | * | 8/2009 |
| JP | 5-238990 A | | 9/1993 |
| JP | 2004-175950 | * | 6/2004 |
| JP | 2004-177668 A | | 6/2004 |
| JP | 2004-303490 | * | 10/2004 |
| JP | 2008-020842 | * | 1/2008 |

(Continued)

OTHER PUBLICATIONS

Lin et al. "Solution-processed hexazatriphenylene hexacarbonitrile as a universal; hole-injection layer for organic light-emitting diodes", Organ. Electron., vol. 14 pp. 1204-1210 (Feb. 2013).*
Gao et al. Synthesis and crosslinking of poly(aryl ether)s contyai9ning 1,1-diphenylethylene moieties., J. Polymer. Sci., Pt A, Polym. Chem., vol. 33 pp. 2347-2352 (1995).*
Qun-Sheng Guo, et al., "A facile synthesis of 3 or 3,3'—substituted binaphthols and their applications in the asymmetric addition of diethylzinc to aldehydes" Journal of Organometallic Chemistry, vol. 691, 2006, pp. 1282-1287.

(Continued)

*Primary Examiner* — Martin Angerbranndt
(74) *Attorney, Agent, or Firm* — Oblon, McClelland, Maier & Neustadt, L.L.P.

(57) ABSTRACT

A composition comprises: a compound having one partial structure represented by formula (1), and a solvent. n1 and n2 are each independently an integer of 0 to 2; and k1 and k2 are each independently an integer of 0 to 9. The compound preferably has an intermolecular bond-forming group. The compound is preferably represented by formula (2). Z represents the partial structure represented by the formula (1); $Ar^1$ and $Ar^2$ represent a substituted or unsubstituted arenediyl group having 6 to 20 carbon atoms; $Ar^3$ and $Ar^4$ represent a substituted or unsubstituted aryl group having 6 to 20 carbon atoms; and p1 and p2 are each independently an integer of 0 to 3.

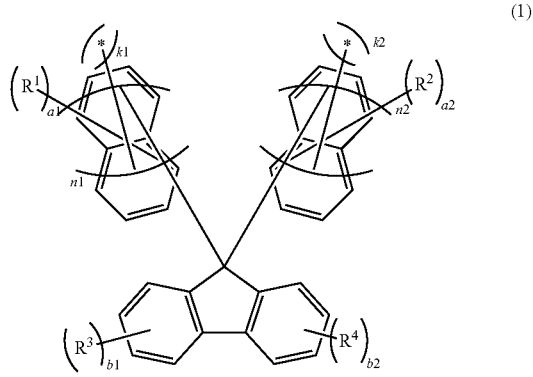

(1)

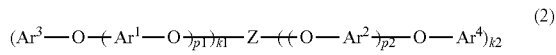

(2)

15 Claims, No Drawings

(56) References Cited

FOREIGN PATENT DOCUMENTS

| | | | |
|---|---|---|---|
| JP | 2013-209571 | * | 10/2013 |
| WO | 2014/157676 | * | 2/2014 |

OTHER PUBLICATIONS

Yasmeen Badar, et al., "Optical Activity in the 1,1'—Binaphthyl Series. Optically Active 8,8'- Dimethyl-1,1' — binaphthyl" Journal of the Chemical Society, 1965, pp. 1412-1418.

Jen-Chieh Hsieh, et al., "*O*-Dihaloarenes as aryne precursors for nickel-catalyzed [2 + 2 + 2]cycloaddition with alkynes and nitriles" Chem. Commun., 2008, pp. 2992-2994.

R. G. R. Bacon, et al., "Cyclisations with Hydrazine. Part III. Syntheses of Pentaphene and Dinaphtho[2,1-*d*: 1',2' —*f*] [1,2] diazocine" Journal of the Chemical Society, 1963, pp. 839-845.

Katsuhisa Mizoguchi, et al., "Negative-Working Photosensitive Poly(phenylene ether) Based on Poly(2,6-dimethyl-1,4-phenylene ether), a Cross-Linker, and a Photoacid Generator" Macromolecules, vol. 43, No. 6, 2010, pp. 2832-2839.

Katsuhisa Mizoguchi, et al., "Direct Patterning of Poly(ether ether sulfone) Using a Cross-linker and a Photoacid Generator" Polymer Journal, vol. 40, No. 7, 2008, pp. 645-650.

Katsuhisa Mizoguchi, et al., "Negative-Type Photosensitive Poly(phenylene ether) Based on Poly(2,6-dimethyl-1,4-phenylene ether),a Crosslinker, and a Photoacid Generator" Journal of Polymer Science, Part A: Polymer Chemistry, vol. 46, 2008, pp. 4949-4958.

* cited by examiner

COMPOSITION FOR FILM FORMATION, FILM, PRODUCTION METHOD OF PATTERNED SUBSTRATE, AND COMPOUND

BACKGROUND OF THE INVENTION

Field of Invention

The present invention relates to a composition for film formation, a film, a production method of a patterned substrate, and a compound.

Description of the Related Art

In manufacturing semiconductor devices, multilayer resist processes have been employed for attaining a high degree of integration. In these processes, a composition for resist underlayer film formation is first coated on a substrate to provide a resist underlayer film, and then a resist composition is coated on the resist underlayer film to provide a resist film. Thereafter, the resist film is exposed through a mask pattern or the like, and developed with an appropriate developer solution to form a resist pattern. Subsequently, the resist underlayer film is dry-etched using the resist pattern as a mask, and further the substrate is dry-etched using the resulting resist underlayer film pattern as a mask, thereby enabling a desired pattern to be formed on the substrate. Resist underlayer films used in such multilayer resist processes are required to have optical characteristics such as the refractive index and the extinction coefficient, as well as general characteristics such as etching resistance.

The multilayer resist processes involving a procedure of forming a hard mask as an intermediate layer on the resist underlayer film has been studied recently. Specifically, since an inorganic hard mask is formed on a resist underlayer film using a CVD technique according to this procedure, particularly in a case where a nitride inorganic hard mask is formed, the temperature is elevated to be as high as at least 300° C., and typically no less than 400° C., and thus, the resist underlayer film is required to have superior heat resistance. When the resist underlayer film has insufficient heat resistance, a component in the resist underlayer film may be sublimated and the sublimated component may adhere to the substrate again, resulting in a disadvantage of a decrease in yields of the production of semiconductor devices.

Still further, patterns are more frequently formed recently on a substrate having a plurality of types of trenches, in particular trenches having aspect ratios that differ from each other, and the resist underlayer film formed is desired to sufficiently fill these trenches and also have superior flatness.

To meet these demands, structures of polymers, etc., to be contained in a composition, and functional groups included in the polymers have been extensively investigated (see Japanese Unexamined Patent Application, Publication No. 2004-177668). However, it has been still impossible to sufficiently meet the demands described above, according to the conventional compositions described above.

PRIOR ART DOCUMENTS

Patent Documents

Patent Document 1: Japanese Unexamined Patent Application, Publication No. 2004-177668

SUMMARY OF THE INVENTION

Problems to be Solved by the Invention

The present invention was made in view of the foregoing circumstances, and it is an object of the present invention to provide a composition for film formation capable of forming a film having superior heat resistance and flatness while general characteristics such as etching resistance are maintained.

Means for Solving the Problems

An invention made for solving the aforementioned problems is a composition for film formation containing a compound (hereinafter, may be also referred to as "(A) compound" or "compound (A)") having one partial structure represented by the following formula (1) (hereinafter, may be also referred to as "partial structure (I)"), and a solvent (hereinafter, may be also referred to as "(B) solvent" or "solvent (B)"),

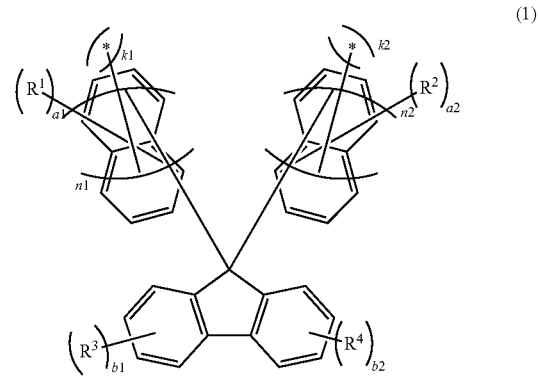

(1)

wherein, in the formula (1), $R^1$ to $R^4$ each independently represent a halogen atom, a hydroxy group, a nitro group or a monovalent organic group having 1 to 20 carbon atoms; a1 and a2 are each independently an integer of 0 to 9; b and b2 are each independently an integer of 0 to 4, wherein in a case where $R^1$ to $R^4$ are each present in a plurality of number, a plurality of $R^1$s may be identical or different, a plurality of $R^2$s may be identical or different, a plurality of $R^3$s may be identical or different, and a plurality of $R^4$s may be identical or different; n1 and n2 are each independently an integer of 0 to 2; k1 and k2 are each independently an integer of 0 to 9, wherein the sum of k1 and k2 is no less than 1, and the sum of a1 and k1 and the sum of a2 and k2 are no greater than 9; and * denotes a binding site to a moiety other than the partial structure.

Another invention made for solving the aforementioned problems is a film formed from the composition for film formation.

Still another invention made for solving the aforementioned problems is a method for producing a patterned substrate including the step of forming a resist underlayer film on an upper face side of a substrate (hereinafter, may be also referred to as "resist underlayer film-forming step"); the step of forming a resist pattern directly or indirectly on the resist underlayer film (hereinafter, may be also referred to as "resist pattern-forming step"), and the step of etching at least the resist underlayer film and the substrate using the resist pattern as a mask such that the substrate has a pattern (hereinafter, may be also referred to as "substrate pattern-forming step"), wherein the resist underlayer film is formed from the composition for film formation described above.

Yet still another invention made for solving the aforementioned problems is a compound having one partial structure represented by the above formula (1).

The "hydrocarbon group" as referred to herein may include a chain hydrocarbon group, an alicyclic hydrocarbon group and an aromatic hydrocarbon group. The "hydrocarbon group" may be either a saturated hydrocarbon group or an unsaturated hydrocarbon group. The "chain hydrocarbon group" refers to a hydrocarbon group that is constituted with only a chain structure without including a cyclic structure, and the "chain hydrocarbon group" may include both a linear chain hydrocarbon group and a branched hydrocarbon group. The "alicyclic hydrocarbon group" as referred to means a hydrocarbon group that includes as a ring structure not an aromatic ring structure but only an alicyclic structure, and the "alicyclic hydrocarbon group" includes both a monocyclic alicyclic hydrocarbon group and a to polycyclic alicyclic hydrocarbon group. However, it is not necessary to be constituted with only an alicyclic structure, and a part thereof may include a chain structure. The "aromatic hydrocarbon group" as referred to means a hydrocarbon group that includes an aromatic ring structure as a ring structure. However, it is not necessary to be constituted with only an aromatic ring structure, and a part thereof may include a chain structure or an alicyclic structure.

Moreover, the "organic group" as referred to means a group that includes at least one carbon atom.

Effects of the Invention

The composition for film formation according to the present invention is capable of forming a film having superior heat resistance and flatness while general characteristics such as etching resistance are maintained. The film is superior in heat resistance and flatness. The method for producing a patterned substrate enables a resist underlayer film having superior heat resistance and flatness to be readily formed, and enables a favorable pattern to be formed on a substrate using the resist underlayer film having such superior characteristics. The compound can be suitably used as a component of the composition for film formation. Therefore, these can be suitably used in manufacture of semiconductor devices, and the like in which further progress of miniaturization is expected in the future.

DESCRIPTION OF THE EMBODIMENTS

Composition for Film Formation

The composition for film formation contains the compound (A) and the to solvent (B). The composition for film formation may contain as a favorable component, (C) an acid generating agent and (D) a crosslinking agent, and may contain other optional component within a range not leading to impairment of the effects of the present invention. Hereinafter, each component will be described.

(A) Compound

The compound (A) is a compound having one partial structure (I). The compound (A) has one partial structure (I), and differs from a polymer having a repeating unit having the partial structure (I). Since the composition for film formation contains the compound (A), a film having superior heat resistance and flatness can be formed while general characteristics such as etching resistance are maintained. Although not necessarily clarified, the reason for the composition for film formation achieving the aforementioned effects due to the composition for film formation having the constitution described above is inferred as follows, for example. Specifically, the compound (A) has the partial structure (I). The partial structure (I) has the specific structure in which two aromatic rings bond to the carbon atom at the 9-position of fluorene skeleton, as shown in the above formula (1). It is inferred that the film formed from the composition for film formation exhibits superior heat resistance due to the specific structure. In addition, since the compound (A) has only one partial structure (I), it is inferred that the molecule size of the compound (A) is suitably small, and consequently the compound (A) can sufficiently fill voids, and thus a film that is superior in flatness can be formed.

Partial Structure (I)

The partial structure (I) is represented by the following formula (1).

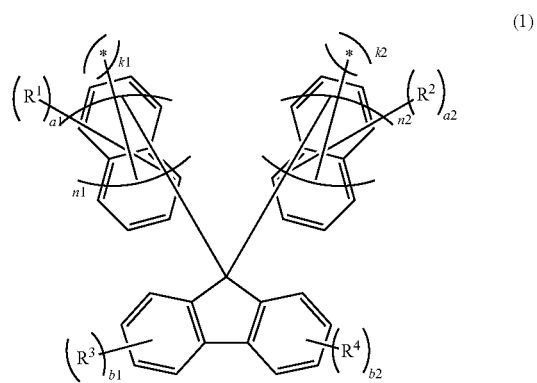

In the above formula (1), $R^1$ to $R^4$ each independently represent a halogen atom, a hydroxy group, a nitro group or a monovalent organic group having 1 to 20 carbon atoms; a1 and a2 are each independently an integer of 0 to 9; b1 and b2 are each independently an integer of 0 to 4, wherein in a case where $R^1$ to $R^4$ are each present in a plurality of number, a plurality of $R^1$s may be identical or different, a plurality of $R^2$s may be identical or different, a plurality of $R^3$s may be identical or different, and a plurality of $R^4$s may be identical or different; n1 and n2 are each independently an integer of 0 to 2; k1 and k2 are each independently an integer of 0 to 9, wherein the sum of k1 and k2 is no less than 1, and the sum of a1 and k1 and the sum of a2 and k2 are no greater than 9; and * denotes a binding site to a moiety other than the partial structure.

Examples of the halogen atom which may be represented by $R^1$ to $R^4$ include a fluorine atom, a chlorine atom, a bromine atom, an iodine atom, and the like.

The monovalent organic group having 1 to 20 carbon atoms which may be represented by $R^1$ to $R^4$ is exemplified by: a monovalent hydrocarbon group having 1 to 20 carbon atoms; a group (α) that includes a divalent hetero atom-containing group between adjacent two carbon atoms of the hydrocarbon group or at an end on the atomic bonding side of the hydrocarbon group; and a group obtained by substituting a part or all of hydrogen atoms included in the hydrocarbon group and the group (α) with a monovalent hetero atom-containing group; and the like.

The monovalent hydrocarbon group having 1 to 20 carbon atoms is exemplified by a monovalent chain hydrocarbon group having 1 to 20 carbon atoms, a monovalent alicyclic hydrocarbon group having 3 to 20 carbon atoms, a monovalent aromatic hydrocarbon group having 6 to 20 carbon atoms, and the like.

Examples of the monovalent chain hydrocarbon group having 1 to 20 carbon atoms include:

alkyl groups such as a methyl group, an ethyl group, a propyl group and a butyl group;

alkenyl groups such as an ethenyl group, a propenyl group, a butenyl group and a pentenyl group;

alkynyl groups such as an ethynyl group, a propynyl group, a butynyl group and a pentynyl group; and the like.

Examples of the monovalent alicyclic hydrocarbon group having 3 to 20 carbon atoms include:

cycloalkyl groups such as a cyclopentyl group, a cyclobutyl group, a cyclopentyl group, a cyclohexyl group, a cyclooctyl group, a cyclodecyl group, a norbornyl group and an adamantyl group;

cycloalkenyl groups such as a cyclopentenyl group, a cyclobutenyl group, a cyclopentenyl group, a cyclohexenyl group, a cyclooctenyl group and a norbornenyl group; and the like.

Examples of the monovalent aromatic hydrocarbon group having 6 to 20 carbon atoms include:

aryl groups such as a phenyl group, a tolyl group, a xylyl group, a naphthyl group and an anthryl group;

aralkyl groups such as a benzyl group, a phenethyl group and a naphthylmethyl group; and the like.

Examples of the hetero atom included in the monovalent hetero atom-containing group and the divalent hetero atom-containing group include an oxygen atom, a nitrogen atom, a sulfur atom, a phosphorus atom, a silicon atom, and the like. Of these, the oxygen atom, the nitrogen atom and the sulfur atom are preferred, and the oxygen atom and the nitrogen atom are more preferred.

Examples of the divalent hetero atom-containing group include —CO—, —CS—, —O—, —NR'—, —S—, and the like, wherein R' represents a monovalent hydrocarbon group having 1 to 10 carbon atoms.

Examples of the monovalent hetero atom-containing group include a halogen atom, a hydroxy group, a sulfanyl group, a carboxy group, a cyano group, a nitro group, and the like.

Moreover, the substituent which may be present on the hydrocarbon group and the group (α) also encompasses an oxygen atom that substitutes for two hydrogen atoms on a single carbon atom of the hydrocarbon group and the group (α).

$R^1$ to $R^4$ represent preferably a halogen atom or a monovalent organic group, more preferably a fluorine atom or a monovalent chain hydrocarbon group, and still more preferably a fluorine atom or an alkyl group.

In light of the heat resistance of the film, a1 and a2 are preferably an integer of 0 to 2, more preferably 0 or 1, and still more preferably 0.

In light of the heat resistance of the film, b1 and b2 are preferably an integer of 0 to 2, more preferably 0 or 1, and still more preferably 0.

In light of achieving both the heat resistance and the flatness of the film at a higher level, n1 and n2 are preferably 0 or 1, and more preferably 1.

In light of an improvement of the flatness of the film, and in light of the ease in synthesis of the compound (A), k1 and k2 are preferably an integer of 0 to 2, more preferably 1 or 2, and still more preferably 1.

The compound (A) preferably has an intermolecular bond-forming group. The "intermolecular bond-forming group" as referred to means a group that can form a covalent bond between molecules through, for example, an addition reaction, a condensation reaction, or the like. When the compound (A) has the intermolecular bond-forming group, the strength of the film can be increased by bonding e.g., between molecules of the compound (A). The compound (A) may have the intermolecular bond-forming group either in the partial structure (I), or in a moiety other than the partial structure (I); however, in light of a further improvement of the heat resistance of the film, the to compound (A) preferably has the intermolecular bond-forming group in the moiety other than the partial structure (I).

The intermolecular bond-forming group is exemplified by a carbon-carbon double bond-containing group, a carbon-carbon triple bond-containing group, a hydroxy chain hydrocarbon group, an acyl group, an acyloxy group, a carbonyloxy hydrocarbon group, an epoxy group, an alkoxymethyl group, a dialkylaminomethyl group, a dimethylolaminomethyl group, and the like. Of these, the carbon-carbon double bond-containing group, the carbon-carbon triple bond-containing group and the acyl group are preferred. The intermolecular bond-forming group is more preferably the carbon-carbon triple bond-containing group or the carbon-carbon double bond-containing group. When the intermolecular bond-forming group is the carbon-carbon triple bond-containing group or the carbon-carbon double bond-containing group, a bond can be formed between the molecules through an addition reaction between carbon-carbon multiple bonds, and curing can occur without the necessity of elimination of any group. Accordingly, a film can be formed while the shrinkage of the film is inhibited, and consequently a film that is more superior in flatness can be formed.

The carbon-carbon double bond-containing group is exemplified by a (meth)acryloyl group, a substituted or unsubstituted vinylphenyl group, a group represented by the following formula (3-1) (hereinafter, may be also referred to as "group (3-1)"), and the like. Moreover, the carbon-carbon triple bond-containing group is exemplified by a substituted or unsubstituted ethynyl group, a substituted or unsubstituted propargyl group, a group represented by the following formula (3-2) (hereinafter, may be also referred to as "group (3-2)"), and the like.

(3-1)

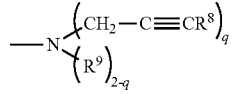
(3-2)

In the above formula (3-1), $R^5$, $R^6$ and $R^7$ each independently represent a hydrogen atom or a monovalent hydrocarbon group having 1 to 20 carbon atoms.

In the above formula (3-2), $R^8$ and $R^9$ each independently represent a hydrogen atom or a monovalent hydrocarbon group having 1 to 20 carbon atoms; and q is 1 or 2, wherein in a case where q is 2, a plurality of $R^8$s may be identical or different.

Examples of the monovalent hydrocarbon group having 1 to 20 carbon atoms which may be represented by $R^5$ to $R^9$ include groups similar to those exemplified in connection with the hydrocarbon group having 1 to 20 carbon atoms which may be represented by $R^1$ to $R^4$, and the like.

In light of an improvement of curing properties of the composition for film formation, $R^5$ represents preferably a hydrogen atom or an alkyl group, and more preferably a hydrogen atom or a methyl group. For the same reason, $R^6$ and $R^7$ each independently represent preferably a hydrogen atom or an alkyl group, and more preferably a hydrogen atom.

In light of an improvement of the curing properties of the composition for film formation, $R^8$ and $R^9$ each independently represent preferably a hydrogen atom or an alkyl group, and more preferably a hydrogen atom.

In light of an improvement of the curing properties of the composition for film formation, q is preferably 2.

Examples of the hydroxy chain hydrocarbon group include: monovalent groups such as a hydroxymethyl group, a 1-hydroxyethyl group, a 1-hydroxypropyl group and a 2-hydroxy-2-propyl group; divalent groups such as a hydroxymethanediyl group, a 1-hydroxy-1,1-ethanediyl group and a 1-hydroxy-1,1-propanediyl group; and the like. Of these, the 1-hydroxyethyl group, the 2-hydroxy-2-propyl group, the hydroxymethanediyl group and the 1-hydroxy-1,1-ethanediyl group are preferred.

Examples of the acyl group include a formyl group, an acetyl group, a propionyl group, a butyryl group, and the like. Of these, the formyl group and the acetyl group are preferred.

Examples of the acyloxy group include a formyloxy group, an acetyloxy group, a propionyloxy group, a butyryloxy group, and the like. Of these, the formyloxy group and the acetyloxy group are preferred.

Examples of the carbonyloxy hydrocarbon group include a methoxycarbonyl group, an ethoxycarbonyl group, a propoxycarbonyl group, a phenoxycarbonyl group, a naphthoxycarbonyl group, and the like. Of these, the methoxycarbonyl group is preferred.

The compound (A) may have either one, or two or more intermolecular bond-forming group(s); however, in light of a further improvement of the heat resistance of the film, the compound (A) preferably has two or more intermolecular bond-forming groups.

It is also preferred that the compound (A) has substantially no intermolecular bond-forming group. When the compound (A) has substantially no intermolecular bond-forming group, the shrinkage of the film in the film formation can be inhibited, and consequently a film that is more superior in flatness can be formed.

The structure of the moiety other than the partial structure (I) is not particularly limited as long as the compound (A) has one partial structure (I). However, the compound (A) is exemplified by a compound represented by the following formula (2), and the like. Since the compound represented by the following formula (2) has an aromatic ether bond, the heat resistance of the film formed from the composition for film formation may be further enhanced.

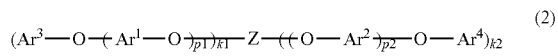
(2)

In the above formula (2), Z represents the partial structure represented by the above formula (1); k1 and k2 are as defined in the above formula (1); $Ar^1$ and $Ar^2$ each independently represent a substituted or unsubstituted arenediyl group having 6 to 20 carbon atoms; $Ar^3$ and $Ar^4$ each independently represent a substituted or unsubstituted aryl group having 6 to 20 carbon atoms; and p1 and p2 are each independently an integer of 0 to 3, wherein in a case where $Ar^1$ to $Ar^4$, p1 and p2 are each present in a plurality of number, a plurality of $Ar^1$s may be identical or different, a plurality of $Ar^2$s may be identical or different, a plurality of $Ar^3$s may be identical or different, a plurality of $Ar^4$s may be identical or different, a plurality of p1s may be identical or different, and a plurality of p2s may be identical or different.

Examples of the arenediyl group having 6 to 20 carbon atoms represented by $Ar^1$ and $Ar^2$ include a benzenediyl group, a toluenediyl group, a xylenediyl group, a naphthalenediyl group, an anthracenediyl group, and the like. Of these, in light of a further improvement of the flatness of the film, the benzenediyl group and the naphthalenediyl group are preferred, and the benzenediyl group is more preferred.

Examples of the substituent which may be present on the arenediyl group represented by $Ar^1$ and $Ar^2$ include halogen atoms such as a fluorine atom, a chlorine atom, a bromine atom and an iodine atom, a hydroxy group, an amino group, a nitro group, a monovalent organic group having 1 to 20 carbon atoms, and the like. Of these, in light of an improvement of the heat resistance of the film and in light of the ease in synthesis of the compound (A), the monovalent organic group having 1 to 20 carbon atoms is preferred, and a cyano group is more preferred.

In light of achieving both the heat resistance and the flatness of the film at a higher level, p1 and p2 are each preferably an integer of 0 to 2, more preferably 1 or 2, and still more preferably 1.

Examples of the aryl group having 6 to 20 carbon atoms represented by $Ar^3$ and $Ar^4$ include a phenyl group, a tolyl group, a xylyl group, a naphthyl group, an anthryl group, and the like.

Examples of the substituent which may be present on the aryl group represented by $Ar^3$ and $Ar^4$ include a halogen atom, a hydroxy group, a nitro group, a monovalent organic group having 1 to 20 carbon atoms, a monovalent intermolecular bond-forming group having 1 to 20 carbon atoms, and the like.

Of these, an aralkyl group having 7 to 20 carbon atoms and the monovalent intermolecular bond-forming group having 1 to 20 carbon atoms are preferred, an aralkyl group having 7 to 12 carbon atoms, the group (3-1) and the group (3-2) are more preferred, and a phenyl-2-propyl group and a di(propargyl)amino group are still more preferred.

Examples of the compound (A) include compounds represented by the following formulae (i-1) to (i-23) (hereinafter, may be also referred to as "compounds (i-1) to (i-23)"), and the like.

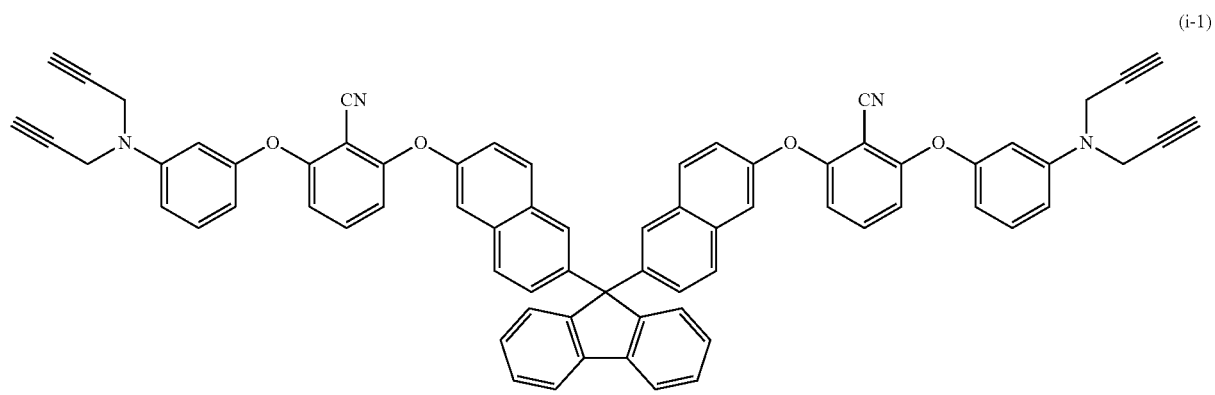
(i-1)
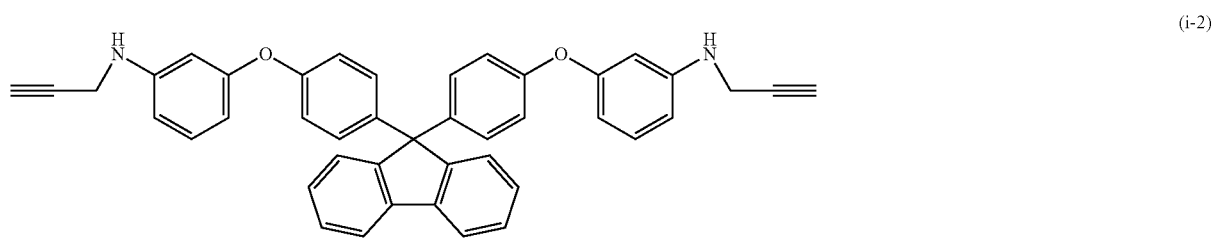
(i-2)
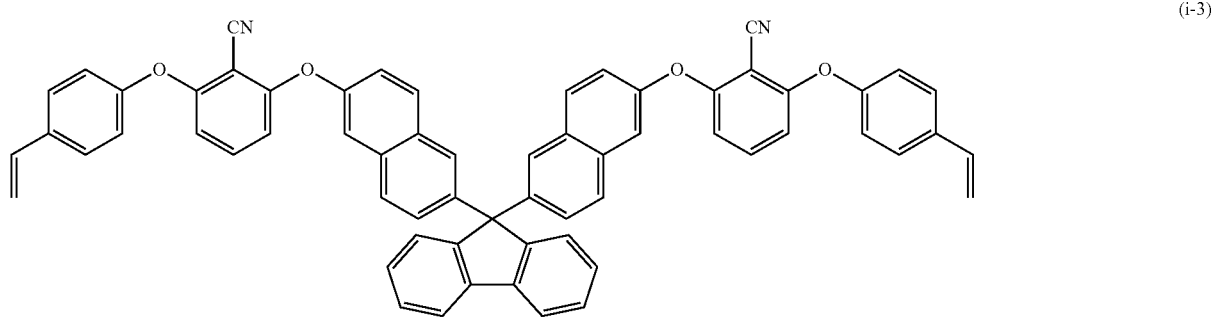
(i-3)
(i-4)
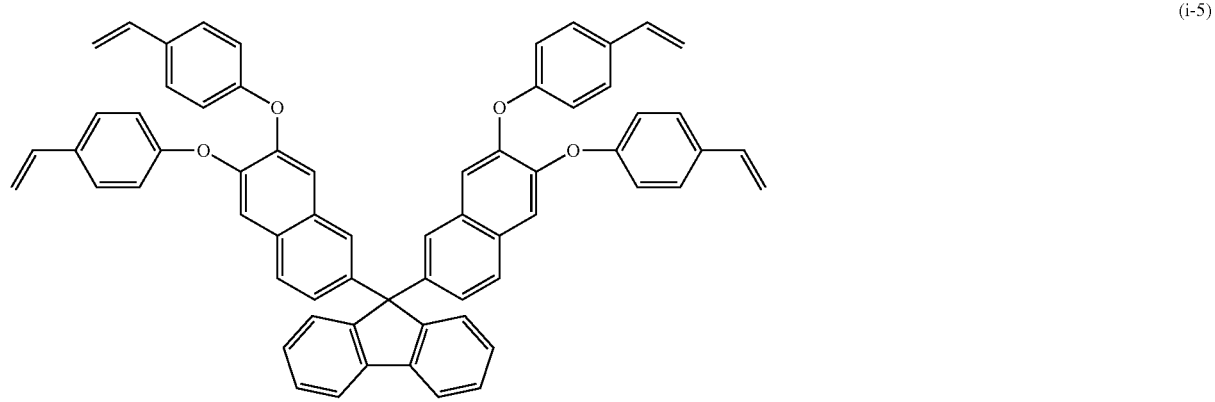
(i-5)

(i-6)
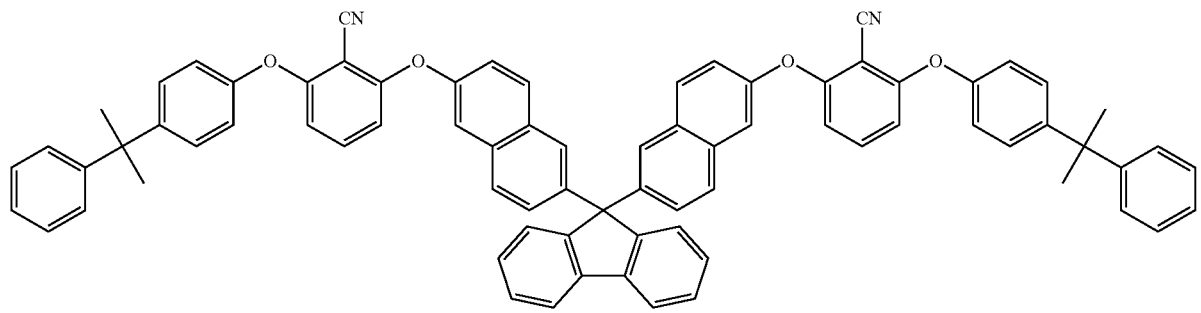
(i-7)
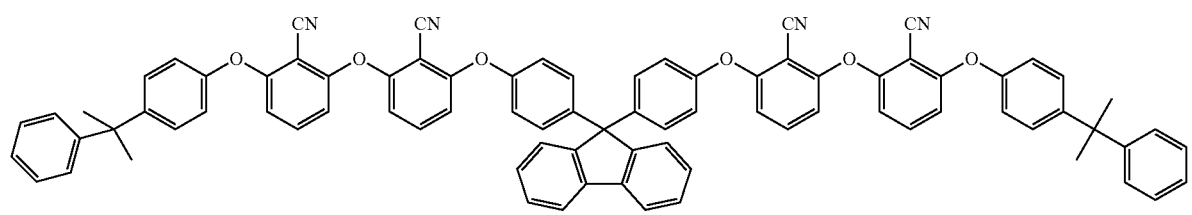
(i-8)
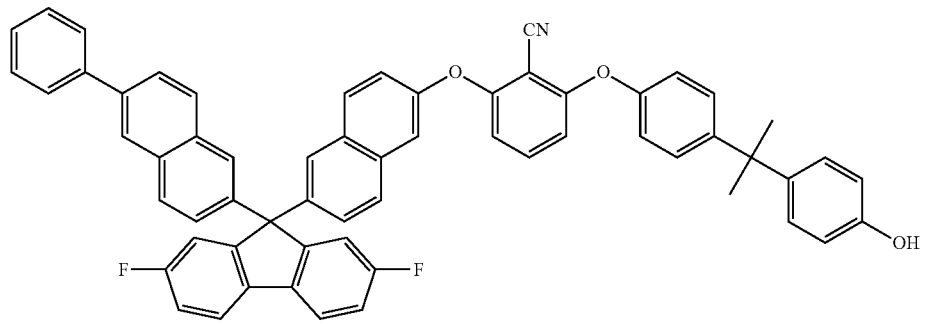
(i-9)
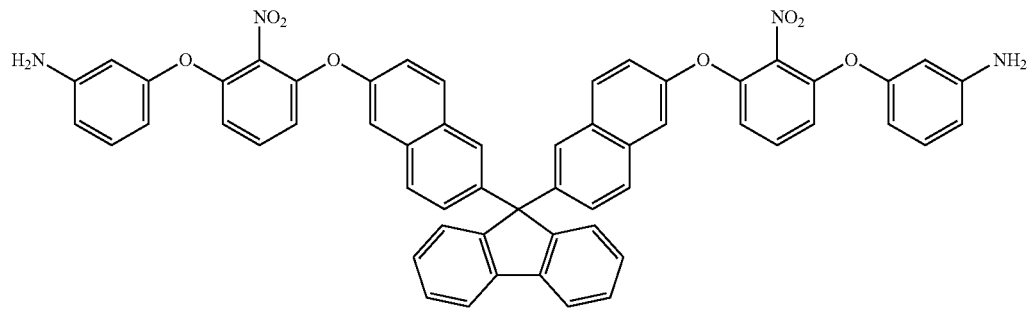
(i-10)
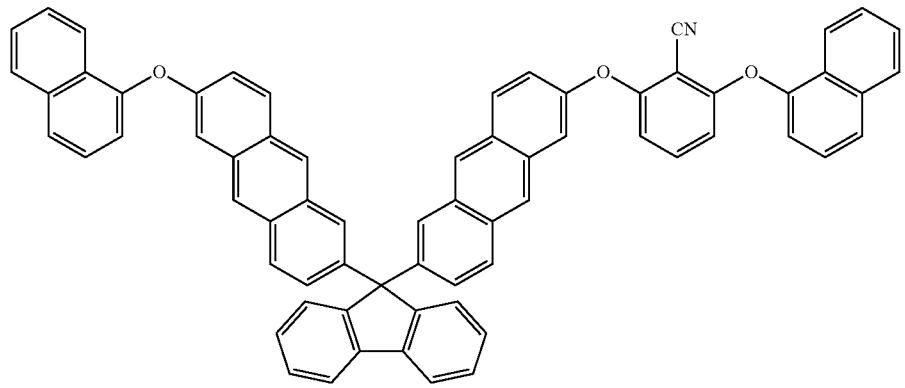

(i-11)
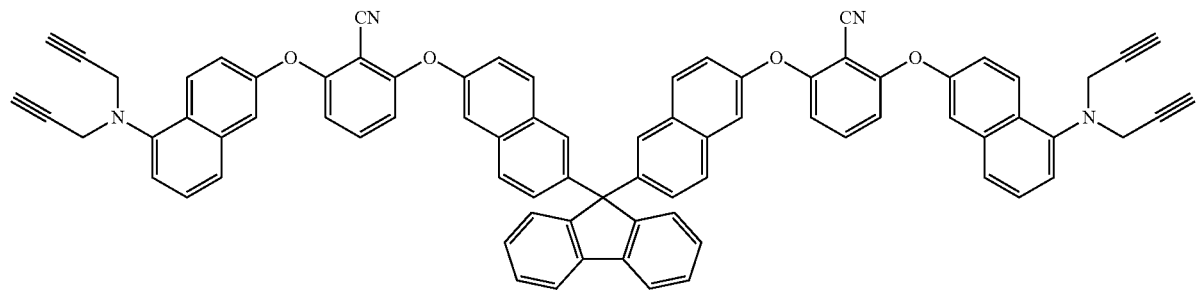
(i-12)
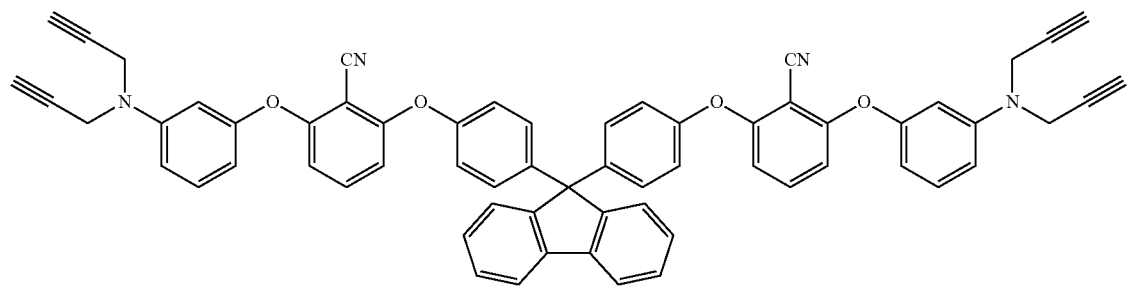
(i-13)
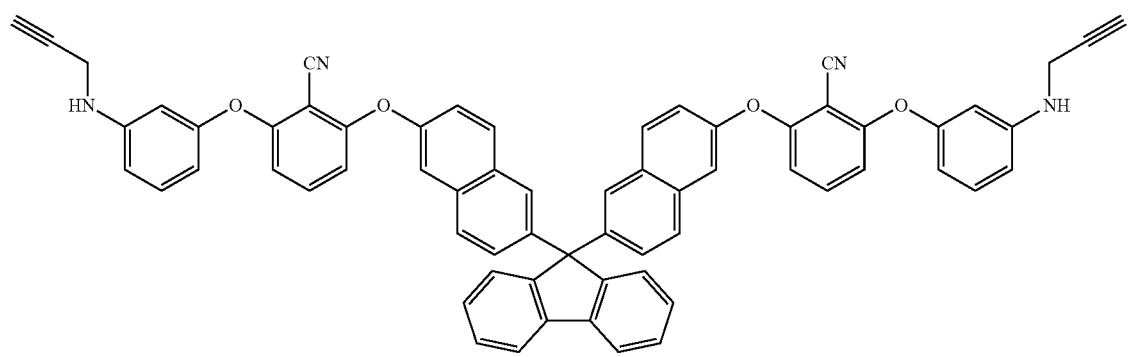
(i-14)
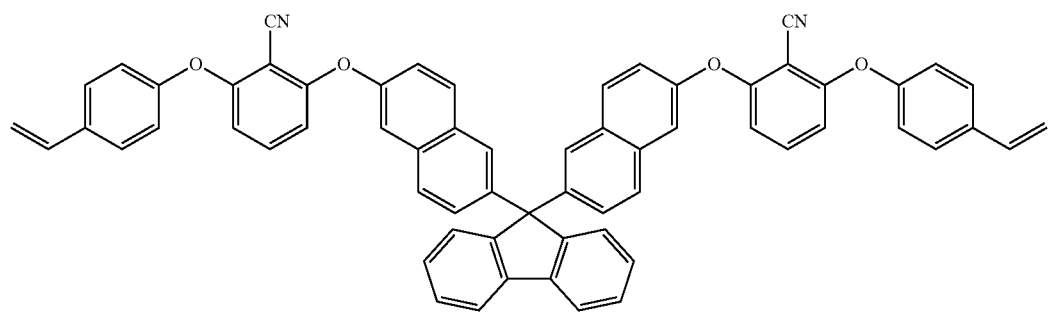
(i-15)
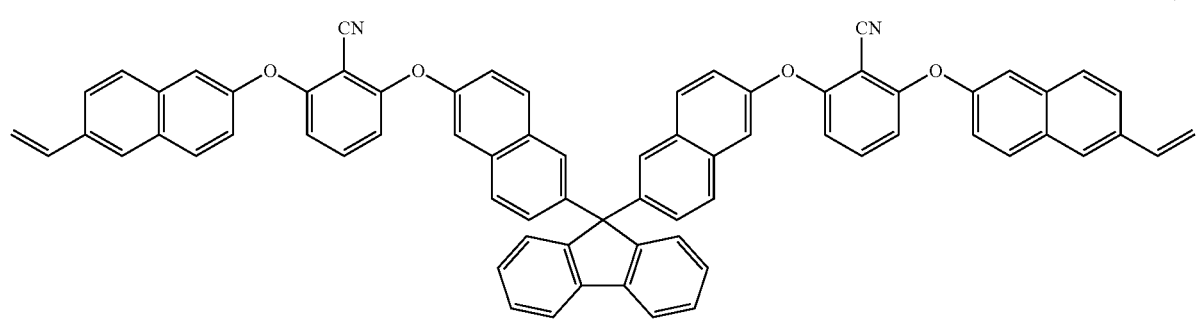

-continued
(i-16)
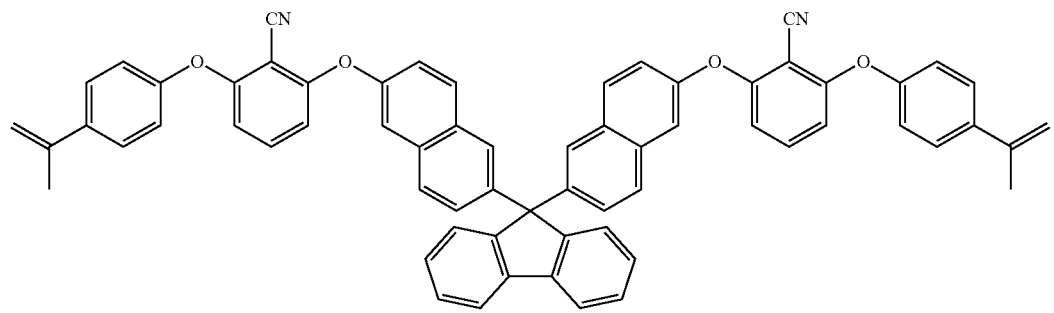
(i-17)
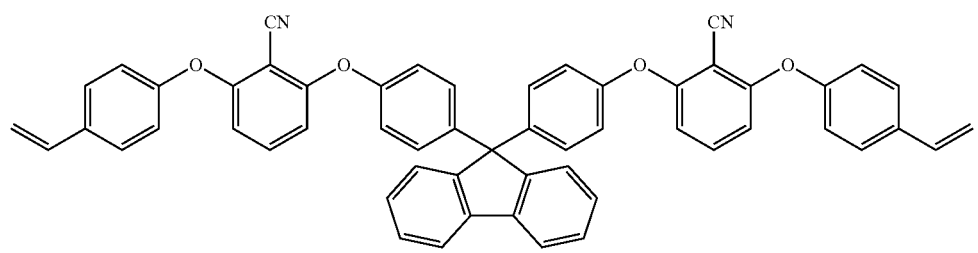
(i-18)
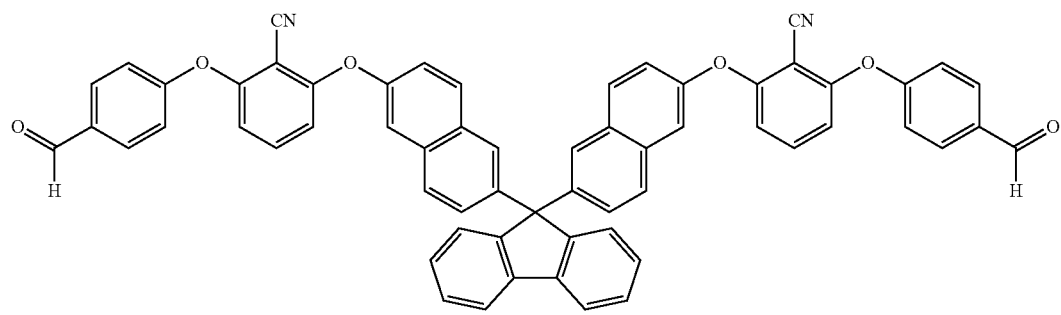
(i-19)
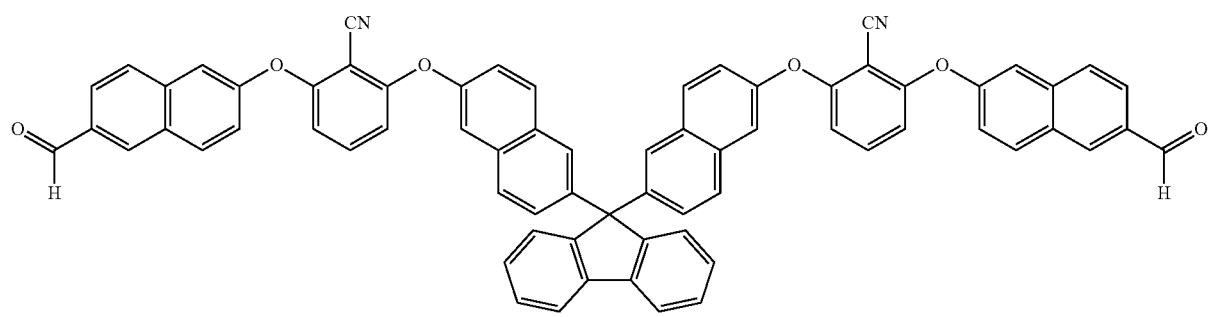
(i-20)
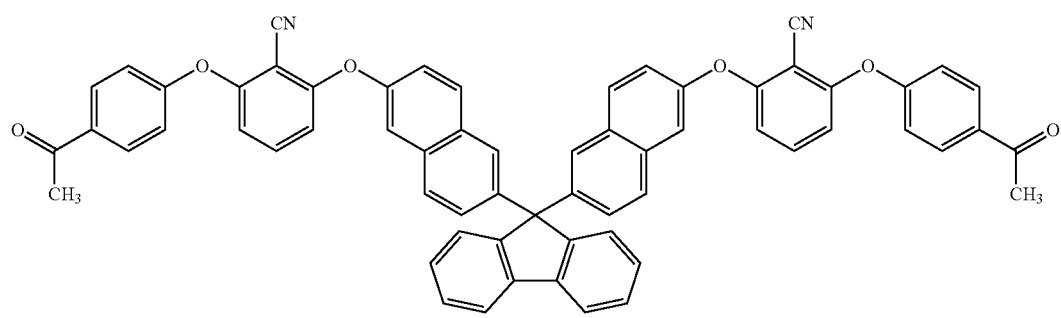

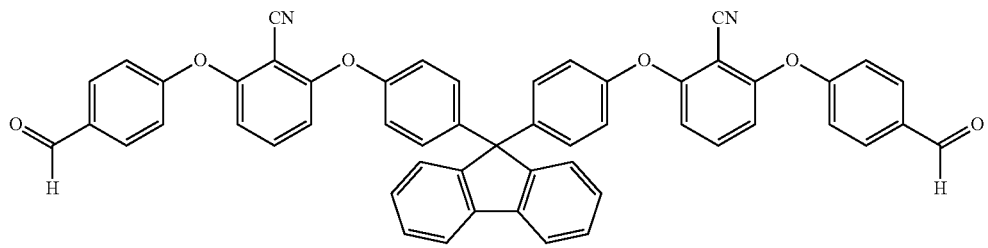

(i-21)

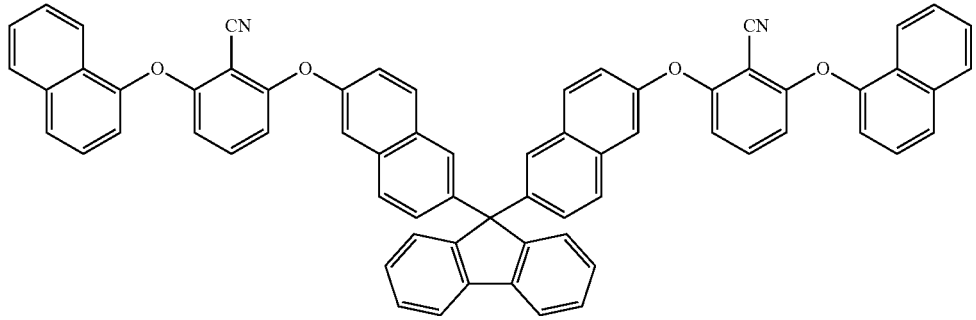

(i-22)

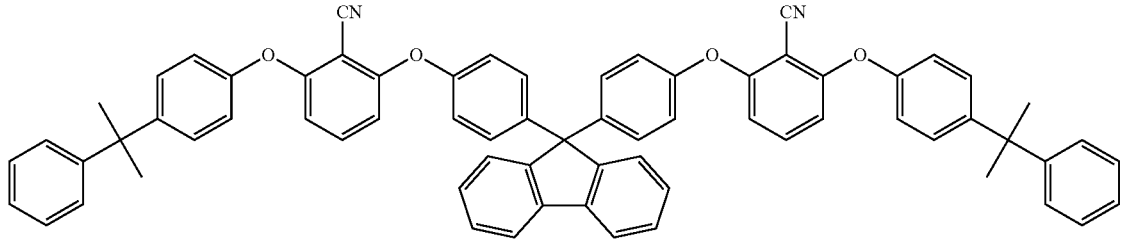

(i-23)

Of these, the compound (i-1), the compound (i-6), and the compounds (i-11) to (i-23) are preferred.

The lower limit of the molecular weight of the compound (A) is preferably 300, more preferably 400, still more preferably 500, and particularly preferably 600. The upper limit of the molecular weight is preferably 3,000, more preferably 2,500, still more preferably 2,000, and particularly preferably 1,500. When the molecular weight of the compound (A) falls within a range between the lower limit and the upper limit, the flatness of the composition for film formation can be further improved.

In light of a further improvement of the heat resistance of the film, the content of the compound (A) is preferably no less than 70% by mass, more preferably no less than 80% by mass, and still more preferably no less than 85% by mass.

Synthesis Method of Compound (A)

The compound (A) can be synthesized by, for example, reacting a polyol component (A) that includes a polyol compound represented by the following formula (4) (hereinafter, may be also referred to as "polyol (4)") with a monohalo component (B) that includes an aromatic monohalide in an organic solvent in the presence of an alkali metal or an alkali metal compound.

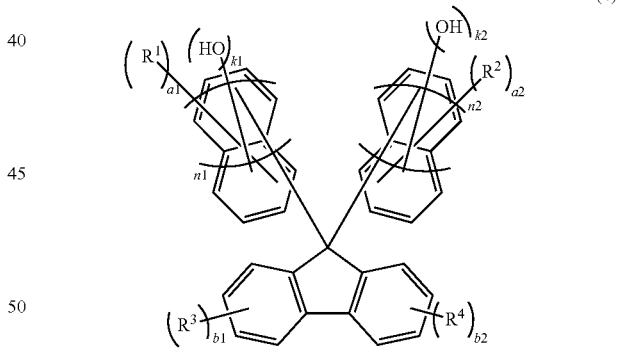

(4)

In the above formula (4), $R^1$ to $R^4$, a1, a2, b1, b2, n1, n2, k1 and k2 are as defined in the above formula (1).

Alternatively, the polyol component (A) may be reacted with an alkali metal or an alkali metal compound in an organic solvent to give an alkali metal salt of the polyol component (A), and then the resulting metal salt may be reacted with the monohalo component (B). The monohalo component (B) can be obtained by, for example, reacting an aromatic dihalo compound with an aromatic monool compound in the presence of a basic compound, etc. The aromatic dihalo compound is exemplified by a compound represented by the following formula (5), and the like.

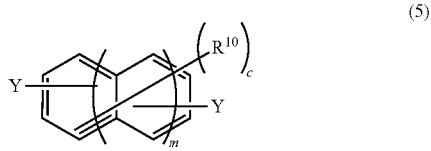

(5)

In the above formula (5), $R^{10}$ represents a nitro group or a monovalent organic group having 1 to 20 carbon atoms; c is an integer of 0 to 8, wherein in a case where $R^{10}$ is present in a plurality of number, a plurality of $R^{10}$s may be identical or different; m is an integer of 0 to 2; and Ys each independently represent a halogen atom.

The aromatic monool compound is exemplified by an unsubstituted or substituted phenol, an unsubstituted or substituted naphthol, and the like. The substituent which may be present on the phenol and the naphthol is exemplified by a phenyl group, a hydroxy group, an amino group, a phenylamino group, the monovalent aralkyl group having 7 to 20 carbon atoms described above, the monovalent intermolecular bond-forming group having 1 to 20 carbon atoms described above, and the like.

Examples of the alkali metal include lithium, sodium, potassium, and the like.

Examples of the alkali metal compound include:

alkali metal carbonates such as lithium carbonate, sodium carbonate and potassium carbonate;

alkali metal hydrogencarbonates such as lithium hydrogencarbonate, sodium hydrogencarbonate and potassium hydrogencarbonate;

alkali metal hydroxides such as lithium hydroxide, sodium hydroxide and potassium hydroxide;

alkali metal hydrides such as lithium hydride, sodium hydride and potassium hydride; and the like.

Of these, the alkali metal carbonates are preferred, and potassium is carbonate is more preferred. These alkali metals and alkali metal compounds may be used either alone of one type, or in combination of two or more types thereof.

It is preferred that an electron-withdrawing group is bound to the aromatic ring of the aromatic dihalide of the dihalo component (B) (for example, $R^{10}$ in the above formula (5) represents an electron-withdrawing group), since the reaction between the component (A) and the component (B) may be facilitated. Examples of the electron-withdrawing group include a cyano group, a nitro group, and the like.

The amount of the alkali metal or the alkali metal compound with respect to the —OH group(s) included in the diol component (A) is preferably 1-fold equivalents to 3-fold equivalents, more preferably 1-fold equivalents to 2-fold equivalents, and still more preferably 1-fold equivalents to 1.5-fold equivalents.

The organic solvent for use in the reaction is exemplified by dimethylacetamide, dimethylformamide, N-methyl-2-pyrrolidone, 1,3-dimethyl-2-imidazolidinone, γ-butyrolactone, sulfolane, dimethyl sulfoxide, diethyl sulfoxide, dimethyl sulfone, diethyl sulfone, diisopropyl sulfone, diphenyl sulfone, diphenyl ether, benzophenone, dialkoxybenzenes (the alkoxy group having 1 to 4 carbon atoms), trialkoxybenzenes (the alkoxy group having 1 to 4 carbon atoms), and the like. Among these solvents, polar organic solvents having a higher relative permittivity, such as N-methyl-2-pyrrolidone, dimethylacetamide, sulfolane, diphenyl sulfone and dimethyl sulfoxide, are preferred. The organic solvents may be used either alone of one type, or in combination of two or more types thereof.

A solvent capable of forming an azeotropic mixture with water, such as benzene, toluene, xylene, hexane, cyclohexane, octane, chlorobenzene, dioxane, tetrahydrofuran, anisole, phenetole, and the like, may be further used in the reaction. These solvents may be used either alone of one type, or in combination of two or more types thereof.

The reaction temperature is preferably 60° C. to 250° C., and more preferably 80° C. to 200° C. The reaction time period is preferably 15 min to 100 hrs, and more preferably 1 hour to 24 hrs.

The synthesized compound may be recovered from the reaction mixture by a reprecipitation technique or the like, and then purified. The solvent for use in the reprecipitation is exemplified by alcohol solvents, and the like. Among these, methanol is preferred.

(B) Solvent

The composition for film formation contains the solvent (B). The solvent (B) is not particularly limited as long as it can dissolve or disperse the compound (A), and the optional component contained as needed.

The solvent (B) is exemplified by an alcohol solvent, a ketone solvent, an amide solvent, an ether solvent, an ester solvent, and the like. The solvent (B) may be used either alone of one type, or in combination of two or more types thereof.

Examples of the alcohol solvent include:

monohydric alcohol solvents such as methanol, ethanol, n-propanol, iso-propanol, n-butanol, iso-butanol, sec-butanol, t-butanol, n-pentanol, iso-pentanol, sec-pentanol and t-pentanol;

polyhydric alcohol solvents such as ethylene glycol, 1,2-propylene glycol, 1,3-butylene glycol, 2,4-pentanediol, 2-methyl-2,4-pentanediol, 2,5-hexanediol and 2,4-heptanediol: and the like.

Examples of the ketone solvent include:

aliphatic ketone solvents such as acetone, methyl ethyl ketone, methyl n-propyl ketone, methyl n-butyl ketone, diethyl ketone, methyl iso-butyl ketone, methyl n-pentyl ketone, ethyl n-butyl ketone, methyl n-hexyl ketone, di-isobutyl ketone and trimethylnonanone;

cyclic ketone solvents such as cyclopentanone, cyclohexanone, cycloheptanone, cyclooctanone and methylcyclohexanone;

2,4-pentanedione, acetonylacetone, diacetone alcohol, acetophenone, and methyl n-amyl ketone; and the like.

Examples of the amide solvent include:

cyclic amide solvents such as 1,3-dimethyl-2-imidazolidinone and N-methyl-2-pyrrolidone;

chain amide solvents such as formamide, N-methylformamide, N,N-dimethylformamide, N,N-diethylformamide, acetamide, N-methylacetamide, N,N-dimethylacetamide and N-methylpropionamide; and the like.

Examples of the ether solvent include:

polyhydric alcohol partial ether solvents such as ethylene glycol monomethyl ether, ethylene glycol monoethyl ether and ethylene glycol dimethyl ether;

polyhydric alcohol partial ether acetate solvents such as ethylene glycol monomethyl ether acetate, ethylene glycol monoethyl ether acetate, propylene glycol monomethyl ether acetate (PGMEA) and propylene glycol monoethyl ether acetate;

dialiphatic ether solvents such as diethyl ether, dipropyl ether, dibutyl ether, butyl methyl ether, butyl ethyl ether and diisoamyl ether;

aliphatic-aromatic ether solvents such as anisole and phenyl ethyl ether;

cyclic ether solvents such as tetrahydrofuran, tetrahydropyran and dioxane; and the like.

Examples of the ester solvent include:

carboxylic acid ester solvents such as methyl lactate, ethyl lactate, methyl acetate, ethyl acetate, n-propyl acetate, iso-propyl acetate, n-butyl acetate, iso-butyl acetate, sec-butyl acetate, n-pentyl acetate, sec-pentyl acetate, 3-methoxybutyl acetate, methylpentyl acetate, 2-ethylbutyl acetate, 2-ethylhexyl acetate, benzyl acetate, cyclohexyl acetate, methylcyclohexyl acetate, n-nonyl acetate, methyl acetoacetate and ethyl acetoacetate;

lactone solvents such as γ-butyrolactone and γ-valerolactone;

carbonic acid ester solvents such as diethyl carbonate and propylene carbonate; and the like.

Of these, the ether solvent, the ketone solvent and the ester solvent are preferred, the ether solvent and the ketone solvent are more preferred, and the ether solvent is still more preferred. The ether solvent is preferably the polyhydric alcohol partial ether acetate solvent or a dialiphatic ether solvent, more preferably the polyhydric alcohol partial ether acetate solvent, still more preferably propylene glycol monoalkyl ether acetate, and particularly preferably PGMEA. The ketone solvent is preferably the aliphatic ketone solvent or the cyclic ketone solvent, more preferably methyl n-pentyl ketone, cyclohexanone or cyclopentanone, and still more preferably cyclohexanone. The ester solvent is preferably the carboxylic acid ester solvent or the lactone solvent, more preferably the carboxylic acid ester solvent, and still more preferably ethyl lactate.

(C) Acid Generating Agent

The acid generating agent (C) is a component that generates an acid by an action of heat and/or light and facilitates the crosslinking of molecules of the compound (A). When the composition for film formation contains the acid generating agent (C), the crosslinking reaction of the compound (A) is facilitated and the hardness of the formed film may be further increased. The acid generating agent (C) may be used either alone of one type, or in combination of two or more types thereof.

The acid generating agent (C) is exemplified by an onium salt compound, an N-sulfonyloxyimide compound, and the like.

The onium salt compound is exemplified by a sulfonium salt, a tetrahydrothiophenium salt, an iodonium salt, and the like.

Examples of the sulfonium salt include triphenylsulfonium trifluoromethanesulfonate, triphenylsulfonium nonafluoro-n-butanesulfonate, triphenylsulfonium perfluoro-n-octanesulfonate, triphenylsulfonium 2-bicyclo[2.2.1]hept-2-yl-1,1,2,2-tetrafluoroethanesulfonate, 4-cyclohexylphenyldiphenylsulfonium trifluoromethanesulfonate, 4-cyclohexylphenyldiphenylsulfonium nonafluoro-n-butanesulfonate, 4-cyclohexylphenyldiphenylsulfonium perfluoro-n-octanesulfonate, 4-cyclohexylphenyldiphenylsulfonium 2-bicyclo[2.2.1]hept-2-yl-1,1,2,2-tetrafluoroethanesulfonate, 4-methanesulfonylphenyldiphenylsulfonium trifluoromethanesulfonate, 4-methanesulfonylphenyldiphenylsulfonium nonafluoro-n-butanesulfonate, 4-methanesulfonylphenyldiphenylsulfonium perfluoro-n-octanesulfonate, 4-methanesulfonylphenyldiphenylsulfonium 2-bicyclo[2.2.1]hept-2-yl-1,1,2,2-tetrafluoroethanesulfonate, and the like.

Examples of the tetrahydrothiophenium salt include 1-(4-n-butoxynaphthalen-1-yl)tetrahydrothiophenium trifluoromethanesulfonate, 1-(4-n-butoxynaphthalen-1-yl)tetrahydrothiophenium nonafluoro-n-butanesulfonate, 1-(4-n-butoxynaphthalen-1-yl)tetrahydrothiophenium perfluoro-n-octanesulfonate, 1-(4-n-butoxynaphthalen-1-yl)tetrahydrothiophenium 2-bicyclo[2.2.1]hept-2-yl-1,1,2,2-tetrafluoroethanesulfonate, 1-(6-n-butoxynaphthalen-2-yl)tetrahydrothiophenium trifluoromethanesulfonate, 1-(6-n-butoxynaphthalen-2-yl)tetrahydrothiophenium nonafluoro-n-butanesulfonate, 1-(6-n-butoxynaphthalen-2-yl)tetrahydrothiophenium perfluoro-n-octanesulfonate, 1-(6-n-butoxynaphthalen-2-yl)tetrahydrothiophenium 2-bicyclo[2.2.1]hept-2-yl-1,1,2,2-tetrafluoroethanesulfonate, 1-(3,5-dimethyl-4-hydroxyphenyl)tetrahydrothiophenium trifluoromethanesulfonate, 1-(3,5-dimethyl-4-hydroxyphenyl)tetrahydrothiophenium nonafluoro-n-butanesulfonate, 1-(3,5-dimethyl-4-hydroxyphenyl)tetrahydrothiophenium perfluoro-n-octanesulfonate, 1-(3,5-dimethyl-4-hydroxyphenyl)tetrahydrothiophenium 2-bicyclo[2.2.1]hept-2-yl-1,1,2,2-tetrafluoroethanesulfonate, and the like.

Examples of the iodonium salt include diphenyliodonium trifluoromethanesulfonate, diphenyliodonium nonafluoro-n-butanesulfonate, diphenyliodonium perfluoro-n-octanesulfonate, diphenyliodonium 2-bicyclo[2.2.1]hept-2-yl-1,1,2,2-tetrafluoroethanesulfonate, bis(4-t-butylphenyl)iodonium trifluoromethanesulfonate, bis(4-t-butylphenyl)iodonium nonafluoro-n-butanesulfonate, bis(4-t-butylphenyl)iodonium perfluoro-n-octanesulfonate, bis(4-t-butylphenyl)iodonium 2-bicyclo[2.2.1]hept-2-yl-1,1,2,2-tetrafluoroethanesulfonate, and the like.

Examples of the N-sulfonyloxyimide compound include N-(trifluoromethanesulfonyloxy)bicyclo[2.2.1]hept-5-ene-2,3-dicarboxyimide, N-(nonafluoro-n-butane sulfonyloxy) bicyclo[2.2.1]hept-5-ene-2,3-dicarboxyimide, N-(perfluoro-n-octanesulfonyloxy)bicyclo[2.2.1]hept-5-ene-2,3-dicarboxyimide, N-(2-bicyclo[2.2.1]hept-2-yl-1,1,2,2-tetrafluoroethanesulfonyloxy)bicyclo[2.2.1]hept-5-ene-2,3-dicarboxyimide, and the like.

Of these, the acid generating agent (C) is preferably an onium salt compound, more preferably an iodonium salt, and still more preferably bis(4-t-butylphenyl)iodonium nonafluoro-n-butanesulfonate.

The content of the acid generating agent (C) with respect to 100 parts by mass of the compound (A) is preferably 0 parts by mass to 20 parts by mass, more preferably 1 part by mass to 15 parts by mass, and still more preferably 3 parts by mass to 10 parts by mass. When the content of the acid generating agent (C) falls within the above range, the crosslinking reaction of the molecules of the compound (A) may be facilitated more effectively.

(D) Crosslinking Agent

The crosslinking agent (D) is a component that forms a crosslinking bond between components such as the compound (A) in the composition for film formation by an action of heat and/or an acid. Although the compound (A) may have the intermolecular bond-forming group, when the composition for film formation further contains the crosslinking agent (D), the hardness of the film may be further increased. The crosslinking agent (D) may be used either alone of one type, or in combination of two or more types thereof.

The crosslinking agent (D) is exemplified by a polyfunctional (meth)acrylate compound, an epoxy compound, a hydroxymethyl group-substituted phenol compound, an alkoxyalkyl group-containing phenol compound, a compound having an alkoxyalkylated amino group, a random copolymer of an acenaphthylene with hydroxymethylacenaphthylene which is represented by the following formula (6-P), compounds represented by the following formulae (6-1) to (6-12), and the like.

Examples of the polyfunctional (meth)acrylate compound include trimethylolpropane tri(meth)acrylate, ditrimethylolpropane tetra(meth)acrylate, pentaerythritol tri(meth)acrylate, pentaerythritol tetra(meth)acrylate, dipentaerythritol penta(meth)acrylate, dipentaerythritol hexa(meth)acrylate, glycerin tri(meth)acrylate, tris(2-hydroxyethyl)isocyanurate tri(meth)acrylate, ethylene glycol di(meth)acrylate, 1,3-butanediol di(meth)acrylate, 1,4-butanediol di(meth)acrylate, 1,6-hexanediol di(meth)acrylate, neopentyl glycol di(meth)acrylate, diethylene glycol di(meth)acrylate, triethylene glycol di(meth)acrylate, dipropylene glycol di(meth)acrylate, bis(2-hydroxyethyl)isocyanurate di(meth)acrylate, and the like.

Examples of the epoxy compound include novolak epoxy resins, bisphenol epoxy resins, alicyclic epoxy resins, aliphatic epoxy resins, and the like.

Examples of the hydroxymethyl group-substituted phenol compound include 2-hydroxymethyl-4,6-dimethylphenol, 1,3,5-trihydroxymethylbenzene, 3,5-dihydroxymethyl-4-methoxytoluene (i.e., 2,6-bis(hydroxymethyl)-p-cresol), 4,4'-(1-(4-(1-(4-hydroxy-3,5-bis(methoxymethyl)phenyl)-1-methylethyl)phenyl)ethylidene)bis(2,6-bis(methoxymethyl)phenol), and the like.

Examples of the alkoxyalkyl group-containing phenol compound include methoxymethyl group-containing phenol compounds, ethoxymethyl group-containing phenol compounds, and the like.

Examples of the compound having an alkoxyalkylated amino group include nitrogen-containing compounds having a plurality of active methylol groups in a molecule thereof, wherein the hydrogen atom of the hydroxyl group of at least one of the methylol groups is substituted with an alkyl group such as a methyl group or a butyl group, and the like; examples thereof include (poly)methylolated melamines, (poly)methylolated glycolurils, (poly)methylolated benzoguanamines, (poly)methylolated ureas. It is to be noted that a mixture constituted with a plurality of substituted compounds having an alkoxyalkylated amino group may be used as the compound having an alkoxyalkylated amino group, and the compound having an alkoxyalkylated amino group may contain an oligomer component formed through partial self-condensation thereof.

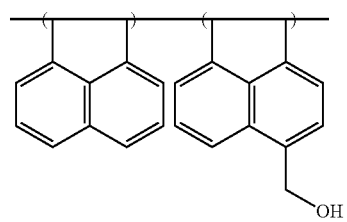

(6-P)

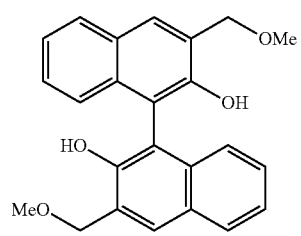

(6-1)

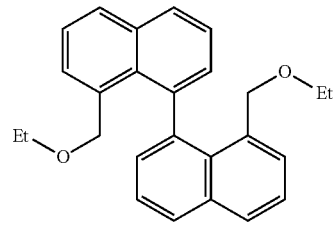

(6-2)

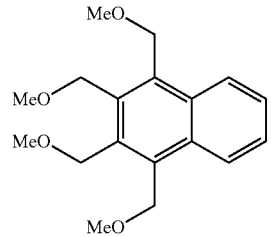

(6-3)

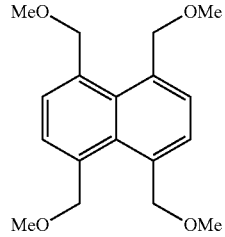

(6-4)

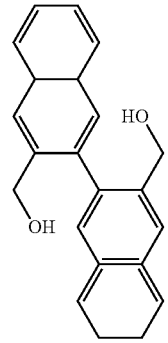

(6-5)

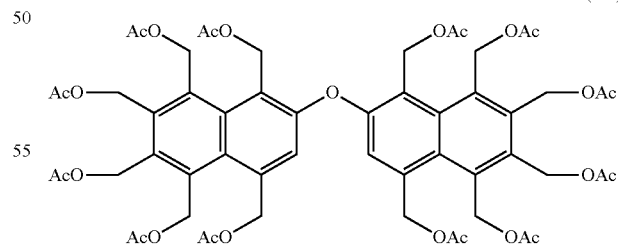

(6-6)

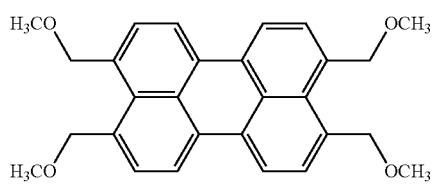

(6-7)

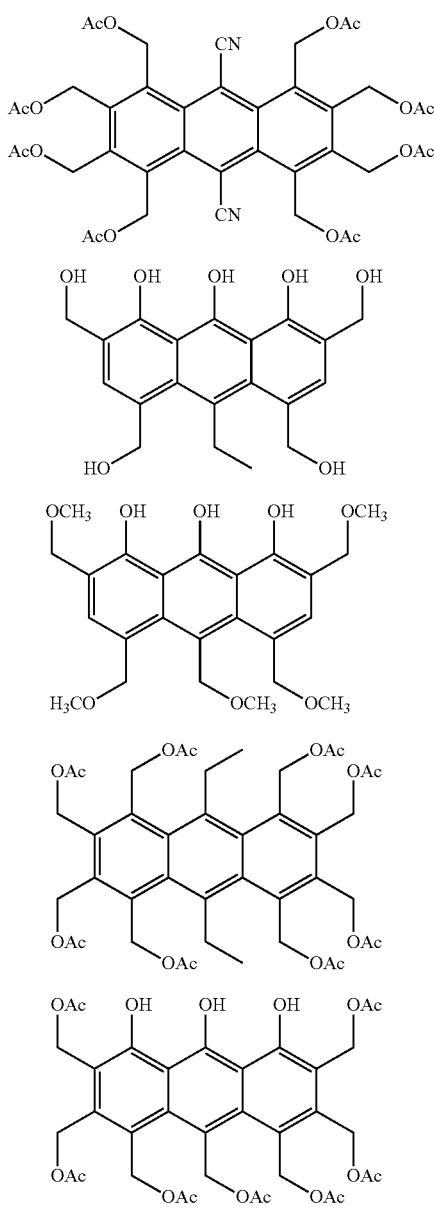

In the above formulae (6-6), (6-8), (6-11) and (6-12), Ac represents an acetyl group.

It is to be noted that the compounds represented by the above formulae (6-1) to (6-12) may be synthesized with reference to the following documents.

The compound represented by the formula (6-1):

Guo, Qun-Sheng; Lu, Yong-Na; Liu, Bing; Xiao, Jian; Li, Jin-Shan, Journal of Organometallic Chemistry, 2006, vol. 691, #6, p. 1282-1287.

The compound represented by the formula (6-2):

Badar, Y. et al., Journal of the Chemical Society, 1965, p. 1412-1418.

The compound represented by the formula (6-3):

Hsieh, Jen-Chieh; Cheng, Chien-Hong, Chemical Communications (Cambridge, United Kingdom), 2008, #26, p. 2992-2994.

The compound represented by the formula (6-4):

Japanese Unexamined Patent Application, Publication No. H5-23 8990.

The compound represented by the formula (6-5):

Bacon, R. G. R.; Bankhead, R., Journal of the Chemical Society, 1963, p. 839-845.

The compounds represented by the formulae (6-6), (6-8), (6-11) and (6-12):

Macromolecules, 2010, vol. 43, p. 2832-2839.

The compounds represented by the formulae (6-7), (6-9) and (6-10):

Polymer Journal, 2008, vol. 40, No. 7, p. 645-650, and Journal of Polymer Science: Part A, Polymer Chemistry, vol. 46, p. 4949-4958.

Among these crosslinking agents (D), the methoxymethyl group-containing phenol compound, the compound having an alkoxyalkylated amino group, a random copolymer of acenaphthylene with hydroxymethylacenaphthylene are preferred, the methoxymethyl group-containing phenol compound and the compound having an alkoxyalkylated amino group are more preferred, and 4,4'-(1-(4-(1-(4-hydroxy-3,5-bis(methoxymethyl)phenyl)-1-methylethyl)phenyl)ethylidene)bis(2,6-bis(methoxymethyl)phenol) and 1,3,4,6-tetra(methoxymethyl)glycoluril are still more preferred.

The content of the crosslinking agent (D) with respect to 100 parts by mass of the compound (A) is preferably 0 to 100 parts by mass, more preferably 0.5 parts by mass to 50 parts by mass, still more preferably 1 part by mass to 30 parts by mass, and particularly preferably 3 parts by mass to no greater than 20 parts by mass. When the content of the crosslinking agent (D) falls within the above range, the hardness of the film may be further increased.

Other Optional Component

Other optional component is exemplified by a surfactant, an adhesion aid, and the like.

Surfactant

When the composition for film formation contains the surfactant, application properties can be improved, and consequently uniformity of the surface of the formed film may be improved and occurrence of the unevenness of coating can be inhibited. The surfactant may be used either alone of one type, or in combination of two or more types thereof.

Examples of the surfactant include nonionic surfactants such as polyoxyethylene lauryl ether, polyoxyethylene stearyl ether, polyoxyethylene oleyl ether, polyoxyethylene n-octylphenyl ether, polyoxyethylene n-nonylphenyl ether, polyethylene glycol dilaurate and polyethylene glycol distearate, and the like. Also, examples of commercially available products include: KP341 (available from Shin-Etsu Chemical Co., Ltd.); Polyflow No. 75 and Polyflow No. 95 (each available from Kyoeisha Chemical Co., Ltd.); EFTOP EF101, EFTOP EF204, EFTOP EF303 and EFTOP EF352 (each available from Tochem Products Co. Ltd.); Megaface F171, Megaface F172 and to Megaface F173 (each available from Dainippon Ink And Chemicals, Incorporated); Fluorad FC430, Fluorad FC431, Fluorad FC135 and Fluorad FC93 (each available from Sumitomo 3M Limited), ASAHI GUARD AG710, Surflon S382, Surflon SC101, Surflon SC102, Surflon SC103, Surflon SC104, Surflon SC105 and Surflon SC106 (each available from Asahi Glass Co., Ltd.); and the like.

The content of the surfactant with respect to 100 parts by mass of the compound (A) is preferably 0 parts by mass to 10 parts by mass, more preferably 0.001 parts by mass to 5 parts by mass, and still more preferably 0.005 parts by mass to no greater than 1 part by mass. When the content of the surfactant falls within the above range, the application properties of the composition for film formation may be further improved.

Adhesion Aid

The adhesion aid is a component that improves adhesiveness to an underlying material. When the composition for film formation contains the adhesion aid, the adhesiveness of the formed film to a substrate, etc., as the underlying material can be improved. The adhesion aid may be used either alone of one type, or in combination of two or more types thereof.

Well-known adhesion aids, for example, may be used as the adhesion aid.

The content of the adhesion aid with respect to 100 parts by mass of the compound (A) is preferably 0 parts by mass to 10 parts by mass, more preferably 0.01 parts by mass to 10 parts by mass, and still more preferably 0.01 parts by mass to 5 parts by mass.

Preparation Method of Composition for Film Formation

The composition for film formation may be prepared by mixing the compound (A) and the solvent (B), and as needed, the acid generating agent (C), the crosslinking agent (D) and other optional component(s) in a predetermined ratio. The solid content concentration of the composition for film formation is preferably 0.1% by mass to 50% by mass, more preferably 1% by mass to 30% by mass, still more preferably 3% by mass to 20% by mass, and particularly preferably 5% by mass to 15% by mass.

The composition for film formation forms the film that is superior in heat resistance and flatness, as described above, and is suitable for film formation. The composition for film formation is particularly suitably used in the formation of a resist underlayer film in multilayer resist processes, etc. for which a higher level of these characteristics is desired, among film formation processes.

Method for Producing Patterned Substrate

A method for producing a patterned substrate according to the present invention includes the resist underlayer film-forming step, the resist pattern-forming step, and the substrate pattern-forming step. The resist underlayer film is formed from the composition for film formation.

According to the method for producing a patterned substrate, a resist underlayer film that is superior in heat resistance and flatness can be readily formed, and a favorable pattern can be formed through the use of the resist underlayer film having such superior characteristics.

Resist Underlayer Film-Forming Step

In this step, a resist underlayer film is formed on an upper face side of a substrate from the composition for film formation. The formation of the resist underlayer film is typically carried out by applying the composition for film formation on the upper face side of the substrate to provide a coating film, and heating the coating film.

Examples of the substrate include a silicon wafer, a wafer coated with aluminum, and the like. Moreover, the method for applying the composition for film formation on the substrate is not particularly limited, and for example, an appropriate process such as a spin-coating process, a cast-coating process, a roll-coating process may be employed.

Heating of the coating film is typically carried out in an ambient air. The heating temperature is typically 150° C. to 500° C., and preferably 200° C. to 450° C. When the heating temperature is less than 150° C., the oxidative crosslinking may not sufficiently proceed, and characteristics necessary for use in the resist underlayer film may not be exhibited. The heating time period is typically 30 sec to 1,200 sec, and preferably 60 sec to 600 sec.

The oxygen concentration in the heating is preferably no less than 5 vol %. When the oxygen concentration in the heating is low, the oxidative crosslinking of the resist underlayer film may not sufficiently proceed, and characteristics necessary for use in the resist underlayer film may not be exhibited.

The coating film may be preheated at a temperature of 60° C. to 250° C. before being heated at a temperature of 150° C. to 500° C. Although the heating time period in the preheating is not particularly limited, the heating time period in the preheating is preferably 10 sec to 300 sec, and more preferably 30 sec to 180 sec. When the preheating is carried out to preliminarily evaporate a solvent and make the film dense, a dehydrogenation reaction may efficiently proceed.

It is to be noted that in the resist underlayer film-forming step, the resist underlayer film is typically formed through the heating of the coating film; however, in a case where the composition for film formation contains a radiation-sensitive acid generating agent, the resist underlayer film may also be formed by hardening the coating film through a combination of an exposure and heating. The radioactive ray used for the exposure may be appropriately selected from visible rays, ultraviolet rays, far ultraviolet rays, X-rays, electron beams, γ radiations, molecular beams, ion beams, and the like in accordance with the type of the radiation-sensitive acid generating agent.

The film thickness of the formed resist underlayer film is preferably 0.05 μm to 5 μm, and more preferably 0.1 μm to 3 μm.

After the resist underlayer film-forming step, the method may further include as needed, the step of forming an intermediate layer (intermediate film) on the resist underlayer film. The intermediate layer as referred to means a layer having a function that is exhibited or not exhibited by the resist underlayer film and/or the resist film in resist pattern formation in order to further enhance the function exhibited by the resist underlayer film and/or the resist film, or to to impart to the resist underlayer film and/or the resist film a function not exhibited thereby. For example, when an antireflective film is provided as the intermediate layer, an antireflecting function of the resist underlayer film may be further enhanced.

The intermediate layer may be formed from an organic compound and/or an inorganic oxide. Examples of the organic compound include commercially available products such as "DUV-42", "DUV-44", "ARC-28" and "ARC-29" (each available from Brewer Science); "AR-3" and "AR-19" (each Lohm and Haas Company); and the like. Examples of the inorganic oxide include commercially available products such as "NFC SOG01", "NFC SOG04" and "NFC SOG080" (each available from JSR Corporation), and the like. Moreover, polysiloxanes, titanium oxides, alumina oxides, tungsten oxides, and the like that are provided through a CVD process may be used.

The method for forming the intermediate layer is not particularly limited, and for example, a coating method, a CVD technique, or the like may be employed. Of these, the coating method is preferred. In a case where the coating method is employed, the intermediate layer may be successively provided after the resist underlayer film is formed. Moreover, the film thickness of the intermediate layer is particularly limited and may be appropriately selected in accordance with the function required for the intermediate layer, and the film thickness is preferably 10 nm to 3,000 nm, and more preferably 20 nm to 300 nm.

Resist Pattern-Forming Step

In this step, a resist pattern is formed directly or indirectly on the resist underlayer film. This step may be carried out, for example, using a resist composition.

When the resist composition is used, specifically, the resist film is formed by applying the resist composition such that the resulting resist film has a predetermined film thickness and thereafter subjecting the resist composition to prebaking to evaporate the solvent in the coating film.

Examples of the resist composition include a chemically amplified positive or negative resist composition that contains a photoacid generating agent; a positive resist composition that is constituted with an alkali-soluble resin and a quinone diazide photosensitizing agent; a negative type resist that contains an alkali-soluble resin and a crosslinking agent; and the like.

The total solid content concentration of the resist composition is typically 1% by mass to 50% by mass. Moreover, the resist composition is generally used for providing a resist film, for example, after being filtered through a filter having a pore size of about 0.2 µm. It is to be noted that a commercially available resist composition may be used as is in this step.

The method for applying the resist composition is not particularly limited, and examples thereof include a spin-coating method, and the like. Moreover, the prebaking temperature may be appropriately adjusted in accordance with the type of the resist composition used, and the like, and the prebaking temperature is typically 30° C. to 200° C., and preferably 50° C. to 150° C.

Next, the resist film formed is exposed by selective irradiation with a radioactive ray. The radioactive ray for use in the exposure may be appropriately selected from visible rays, ultraviolet rays, far ultraviolet rays, X-rays, electron beams, γ radiations, molecular beams, ion beams and the like in accordance with the type of the photoacid generating agent used in the resist composition. Among these, far ultraviolet rays are preferred, a KrF excimer laser beam (248 nm), an ArF excimer laser beam (193 nm), an $F_2$ excimer laser beam (wavelength: 157 nm), a $Kr_2$ excimer laser beam (wavelength: 147 nm), an ArKr excimer laser beam (wavelength: 134 nm), extreme-ultraviolet rays (wavelength: 13 nm, etc.) and the like are more preferred.

Post-baking may be carried out after the exposure for the purpose of improving a resolution, a pattern profile, developability, and the like. The post-baking temperature may be appropriately adjusted in accordance with the type of the resist composition used, and the like, and the post-baking temperature is typically 50° C. to 200° C., and preferably 70° C. to 150° C.

Next, the exposed resist film is developed with a developer solution to form a resist pattern. The developer solution may be appropriately selected in accordance with the type of the resist composition used. In the case of a development with an alkali, examples of the developer solution include an alkaline aqueous solution that contains sodium hydroxide, potassium hydroxide, sodium carbonate, sodium silicate, sodium metasilicate, ammonia, ethylamine, n-propylamine, diethylamine, di-n-propylamine, triethylamine, methyldiethylamine, dimethylethanolamine, triethanolamine, tetramethylammonium hydroxide, tetraethylammonium hydroxide, pyrrole, piperidine, choline, 1,8-diazabicyclo[5.4.0]-7-undecene, 1,5-diazabicyclo[4.3.0]-5-nonene, or the like. An appropriate amount of a water soluble organic solvent, e.g., an alcohol such as methanol and ethanol, a surfactant, and the like may be added to the alkaline aqueous solution.

Alternatively, in the case of a development with an organic solvent, examples of the developer solution include a variety of organic solvents exemplified as the solvent (B) described above, and the like.

A predetermined resist pattern is formed by the development with the developer solution, followed by washing and drying.

In carrying out the resist pattern-forming step, without using the resist composition described above, other process may be employed, for example, a nanoimprint method may be adopted, or a directed self-assembling composition may be used.

Substrate Pattern-Forming Step

In this step, at least the resist underlayer film and the substrate are etched using the resist pattern as a mask such that the substrate has a pattern. In a case where the intermediate layer is not provided, the resist underlayer film and the substrate are subjected to etching sequentially in this order, whereas in a case where the intermediate layer is provided, the intermediate layer, the resist underlayer film and the substrate are subjected to etching sequentially in this order. The etching procedure may be exemplified by dry-etching, wet-etching, and the like. Of these, the dry-etching is preferred. For example, gas plasma such as oxygen plasma and the like may be used in the dry-etching. After the etching, the substrate having a predetermined pattern can be obtained.

Film

The film according to the present invention is formed from the composition for film formation described above. Since the film is formed from the composition for film formation described above, the film is superior in heat resistance and flatness while general characteristics such as etching resistance are maintained. Since the film has the characteristics, the film can be suitably used as a resist underlayer film, and the like.

Compound

The compound according to the present invention has one partial structure (I).

The compound according to the present invention may be suitably used as a component of the composition for film formation described above, and according to the composition for film formation, a film that is superior in heat resistance and flatness can be formed while general characteristics such as etching resistance are maintained. The compound corresponds to the compound (A) contained in the composition for film formation described above, and the explanation has been presented as in the foregoing.

EXAMPLES

Hereinafter, the embodiment of the present invention will be explained in more detail by way of Examples, but the present invention is not in any way limited to these Examples. Each physical property value was determined according to the method described below.

Mw

The Mw of the polymer was determined by gel permeation chromatography using GPC columns (G2000 HXL×2, and G3000 HXL×1) available from Tosoh Corporation, a differential refractometer as a detector, and mono-dispersed polystyrene as a standard under analytical conditions involving a flow rate of 1.0 mL/min, an elution solvent of tetrahydrofuran and a column temperature of 40° C.

Film Thickness

The film thickness was determined by using a spectroscopic ellipsometer ("M2000D" available from J. A. WOOLLAM).

Synthesis of Compound (A)

Example 1

Synthesis of Compound (A-1)

In a separable flask equipped with a thermometer, 15 parts by mass of the following compound (M-1), 18 parts by mass of the compound (M-2), 6 parts by mass of sodium hydride as a basic compound and 100 parts by mass of tetrahydrofuran as a solvent were blended under a nitrogen atmosphere, and then the reaction was allowed to proceed at 0° C. for 3 hrs with stirring to obtain a reaction mixture. This reaction mixture was added to a mixture of methanol and water to permit reprecipitation, and the resulting precipitates were dried to obtain a compound (M-4). Next, the whole quantity of the obtained compound (M-4), 27 parts by mass of the compound (M-3), 19 parts by mass of potassium carbonate as a basic compound and 150 parts by mass of dimethylacetamide as a solvent were blended, and then the condensation reaction was allowed to proceed at 140° C. for 4 hrs with stirring to obtain a reaction mixture. This reaction mixture was filtered, followed by addition of methanol thereto to permit reprecipitation, and the resulting precipitates were dried to obtain a compound (M-5). Thereafter, the whole quantity of the obtained compound (M-5), 32 parts by mass of propargyl bromide, 19 parts by mass of potassium carbonate as a basic compound and 150 parts by mass of dimethylacetamide as a solvent were blended, and then the reaction was allowed to proceed at 60° C. for 4 hrs with stirring to obtain a reaction mixture. This reaction mixture was filtered, followed by addition of methanol thereto to permit reprecipitation, and the resulting precipitates were dried to obtain 50 parts by mass of the following compound (A-1).

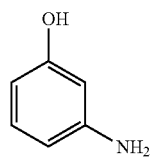

(M-1)

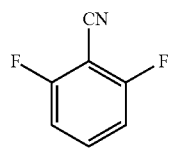

(M-2)

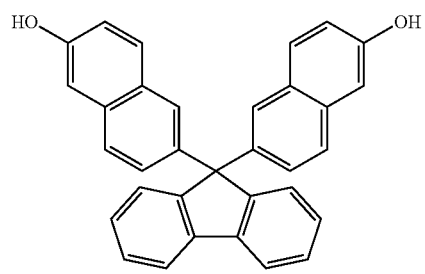

(M-3)

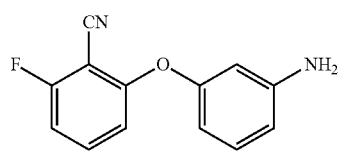

(M-4)

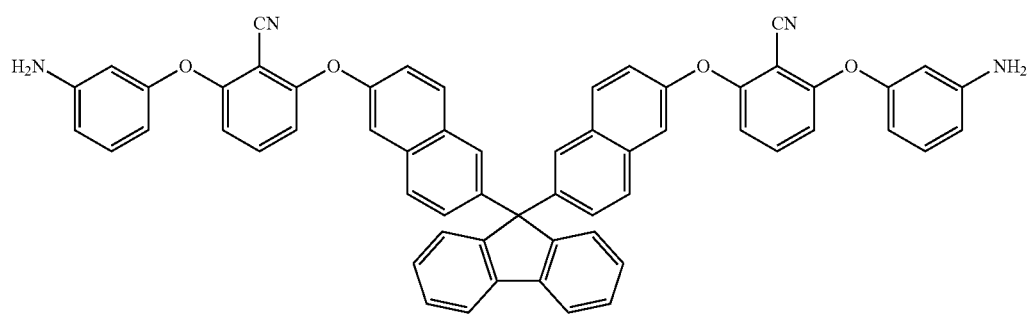

(M-5)

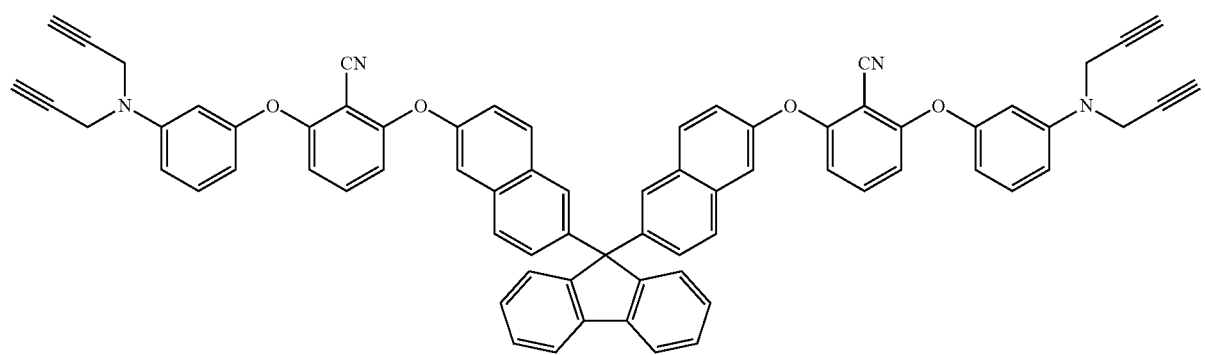
(A-1)
Examples 2 to 4
Synthesis of Compounds (A-2) to (A-4)
The following compounds (A-2), (A-3) and (A-4) were synthesized according to a reaction scheme similar to that for Example 1 except that the materials were changed.
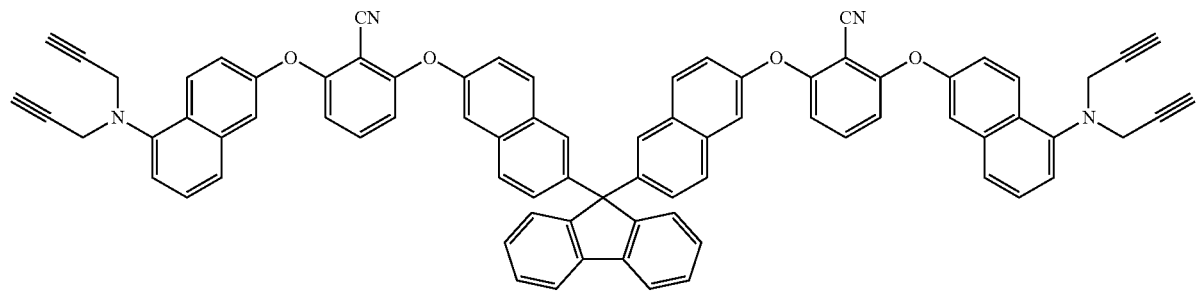
(A-2)
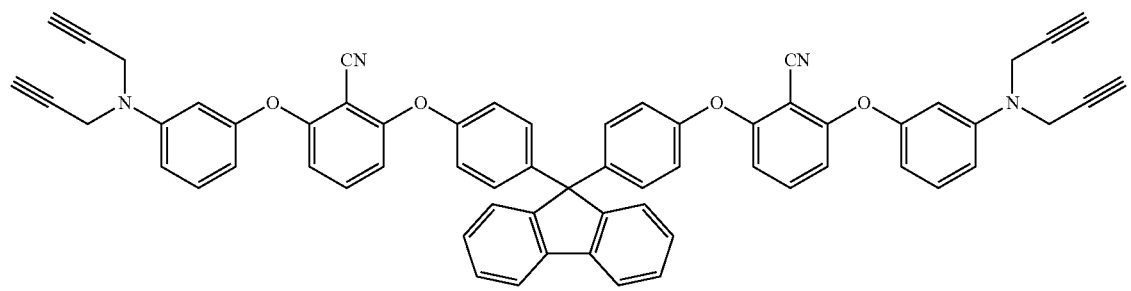
(A-3)
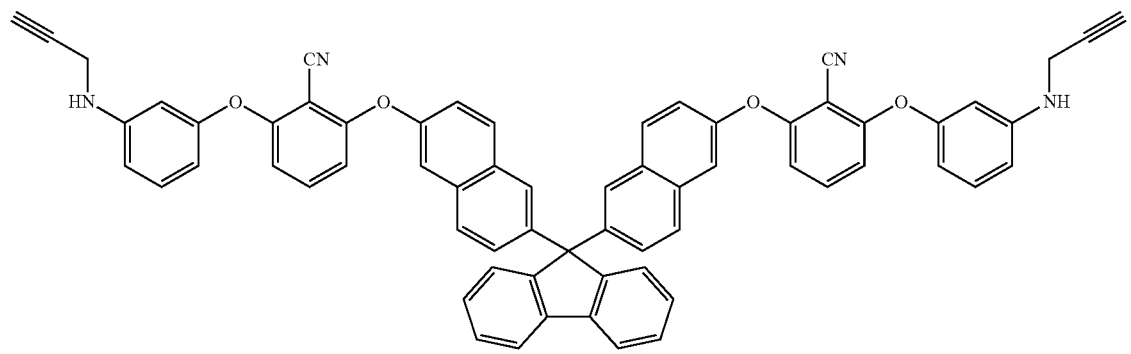
(A-4)

Example 5

Synthesis of Compound (A-5)

In a separable flask equipped with a thermometer, 15 parts by mass of the following compound (M-6), 17 parts by mass of the compound (M-7), 5 parts by mass of sodium hydride as a basic compound and 80 parts by mass of tetrahydrofuran as a solvent were blended under a nitrogen atmosphere, and then the reaction was allowed to proceed at 0° C. for 3 hrs with stirring to obtain a reaction mixture. This reaction mixture was added to a mixture of methanol and water to permit reprecipitation, and the resulting precipitates were dried to obtain a compound (M-9). Thereafter, the whole quantity of the obtained compound (M-9), 24.5 parts by mass of the compound (M-8), 17 parts by mass of potassium carbonate as a basic compound and 140 parts by mass of dimethylacetamide as a solvent were blended, and then the condensation reaction was allowed to proceed at 140° C. for 4 hrs with stirring to obtain a reaction mixture. This reaction mixture was filtered, followed by addition of methanol thereto to permit reprecipitation, and the resulting precipitates were dried to obtain 40 parts by mass of the following compound (A-5).

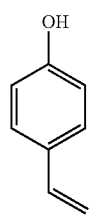
(M-6)

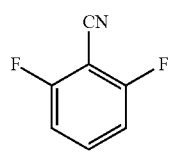
(M-7)

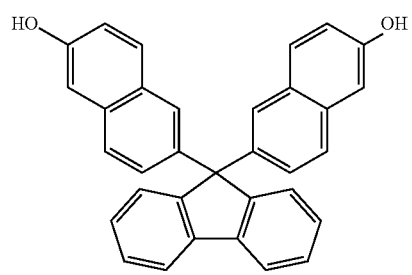
(M-8)

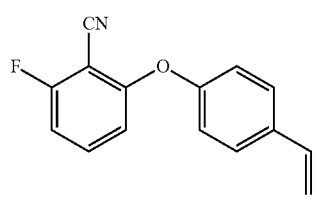
(M-9)

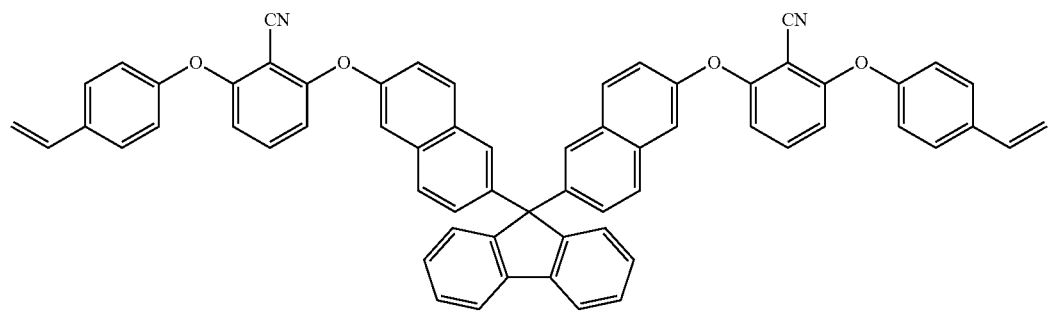
(A-5)

Examples 6 to 8

Synthesis of Compounds (A-6) to (A-8)

The following compounds (A-6), (A-7) and (A-8) were synthesized according to a reaction scheme similar to that for Example 5 except that the materials were changed.

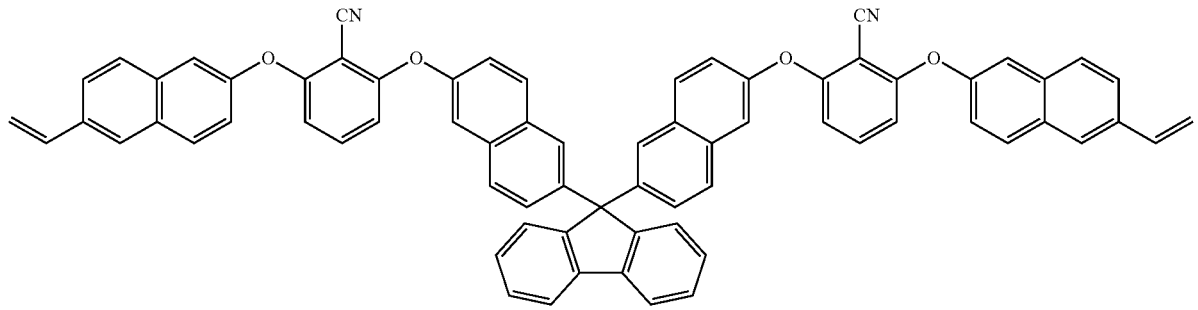

(A-6)

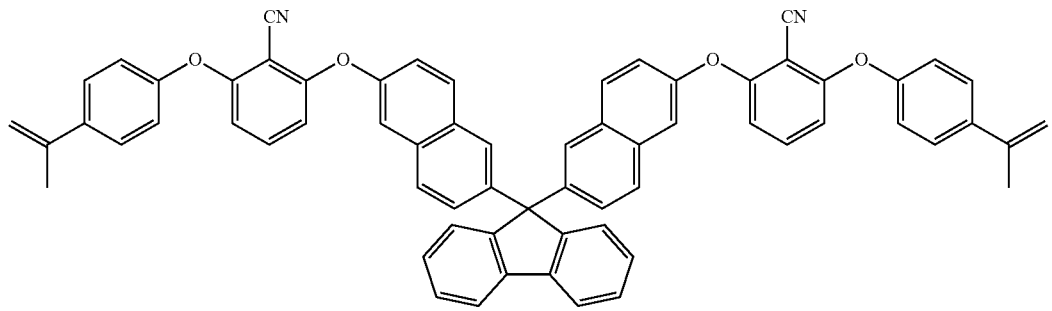

(A-7)

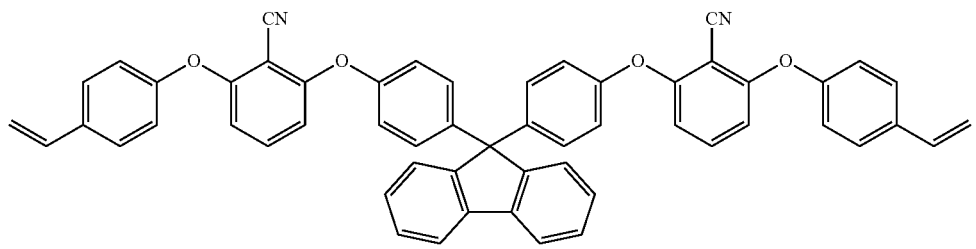

(A-8)

Example 9

Synthesis of Compound (A-9)

In a separable flask equipped with a thermometer, 15 parts by mass of the following compound (M-10), 16.5 parts by mass of the compound (M-11), 5 parts by mass of sodium hydride as a basic compound and 80 parts by mass of tetrahydrofuran as a solvent were blended under a nitrogen atmosphere, and then the reaction was allowed to proceed at 0° C. for 3 hrs with stirring to obtain a reaction mixture. This reaction mixture was added to a mixture of methanol and water to permit reprecipitation, and the resulting precipitates were dried to obtain a compound (M-13). Thereafter, the whole quantity of the obtained compound (M-13), 24 parts by mass of the compound (M-12), 16.5 parts by mass of potassium carbonate as a basic compound and 140 parts by mass of dimethylacetamide as a solvent were blended, and then the condensation reaction was allowed to proceed at 140° C. for 4 hrs with stirring to obtain a reaction mixture. This reaction mixture was filtered, followed by addition of methanol thereto to permit reprecipitation, and the resulting precipitates were dried to obtain 40 parts by mass of the following compound (A-9).

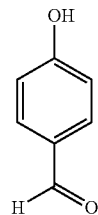
(M-10)

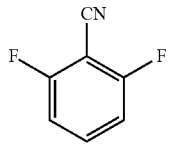
(M-11)

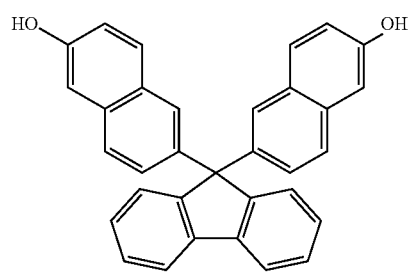
(M-12)

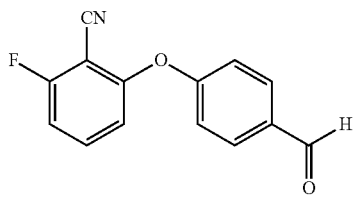
(M-13)

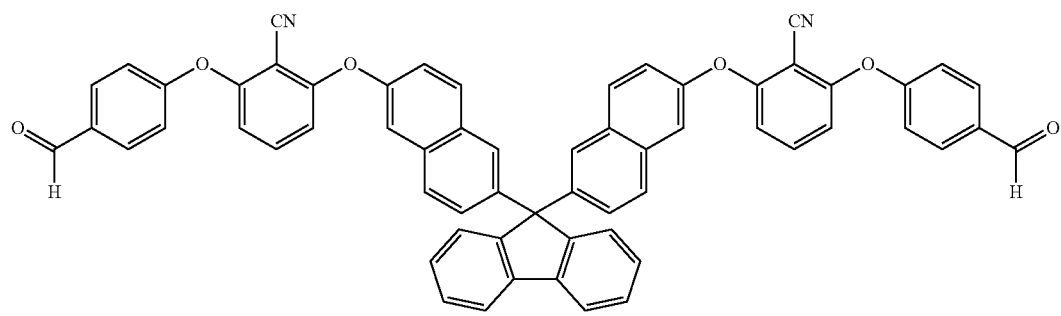
(A-9)

Examples 10 to 12

Synthesis of Compounds (A-10) to (A-12)

The following compounds (A-10), (A-11) and (A-12) were synthesized according to a reaction scheme similar to that for Example 9 except that the materials were changed.

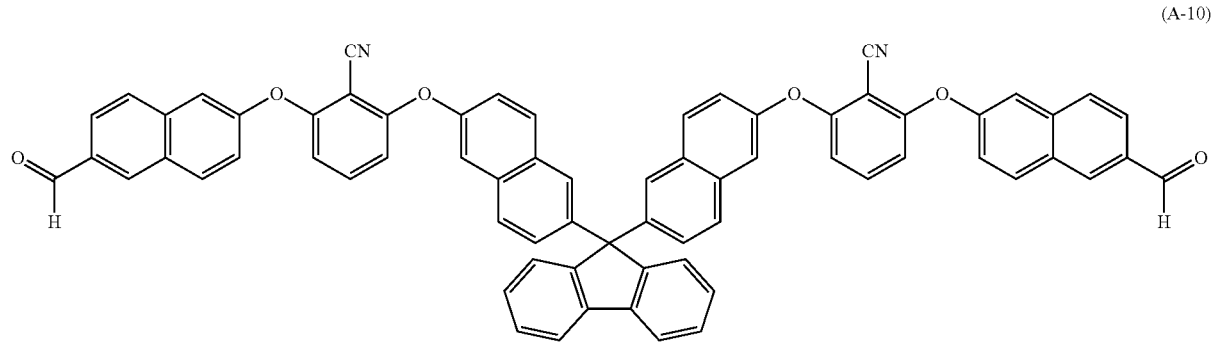
(A-10)

-continued

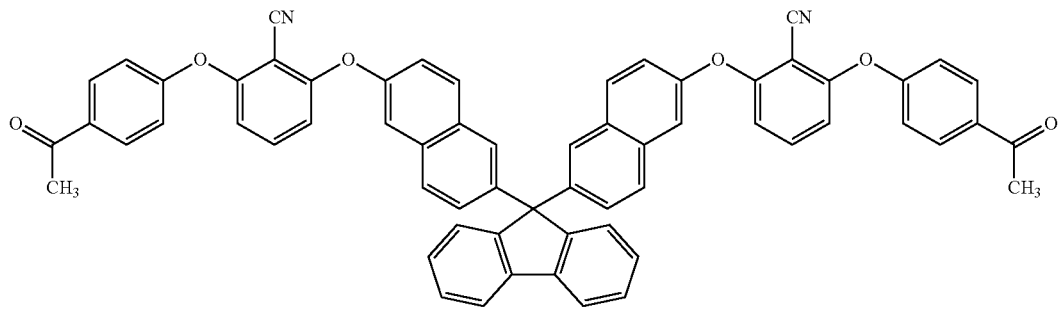
(A-11)

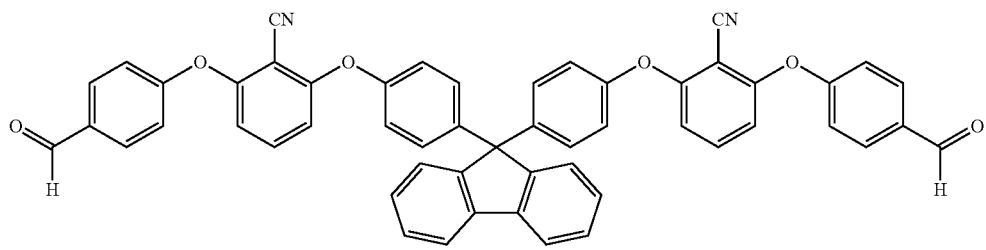
(A-12)

Example 13

Synthesis of Compound (A-13)

In a separable flask equipped with a thermometer, 15 parts by mass of the following compound (M-14), 9.5 parts by mass of the compound (M-15), 3 parts by mass of sodium hydride as a basic compound and 50 parts by mass of tetrahydrofuran as a solvent were blended under a nitrogen atmosphere, and then the reaction was allowed to proceed at 0° C. for 3 hrs with stirring to obtain a reaction mixture. This reaction mixture was added to a mixture of methanol and water to permit reprecipitation, and the resulting precipitates were dried to obtain a compound (M-17). Thereafter, the whole quantity of the obtained (M-17), 14 parts by mass of the compound (M-16), 10 parts by mass potassium carbonate as a basic compound and 80 parts by mass of dimethylacetamide as a solvent were blended, and then the condensation reaction was allowed to proceed at 140° C. for 4 hrs with stirring to obtain a reaction mixture. This reaction mixture was filtered, followed by addition of methanol thereto to permit reprecipitation, and the resulting precipitates were dried to obtain 28 parts by mass of the following compound (A-13).

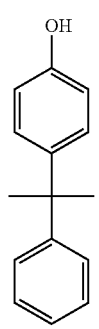
(M-14)

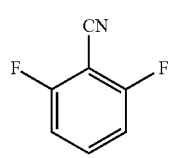
(M-15)

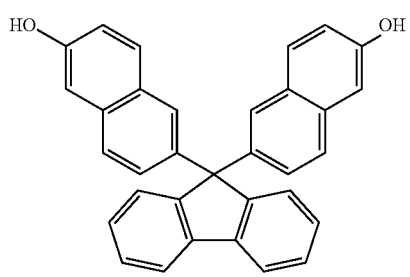
(M-16)

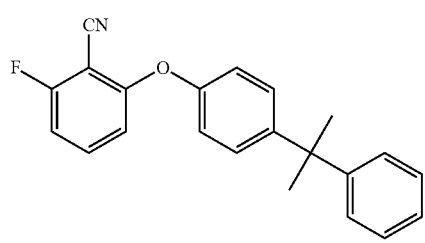
(M-17)

(A-13)

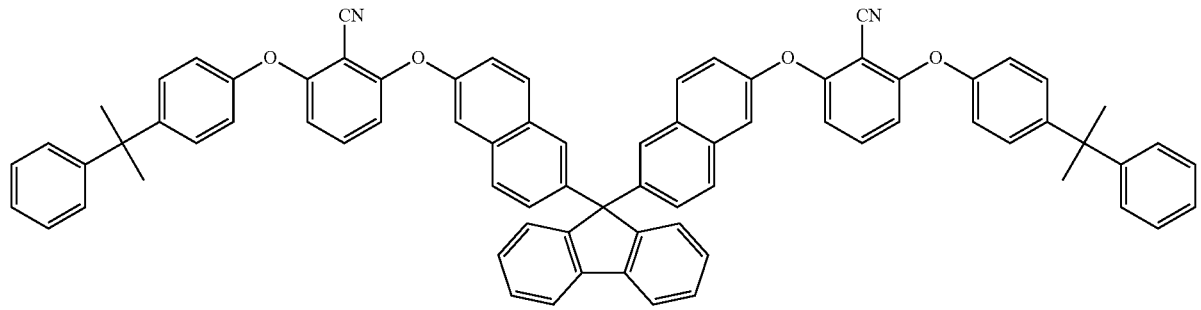

Examples 14 and 15

Synthesis of Compounds (A-14) and (A-15)

The following compounds (A-14) and (A-15) were synthesized according to a reaction scheme similar to that for Example 13 except that the materials were changed.

(A-14)

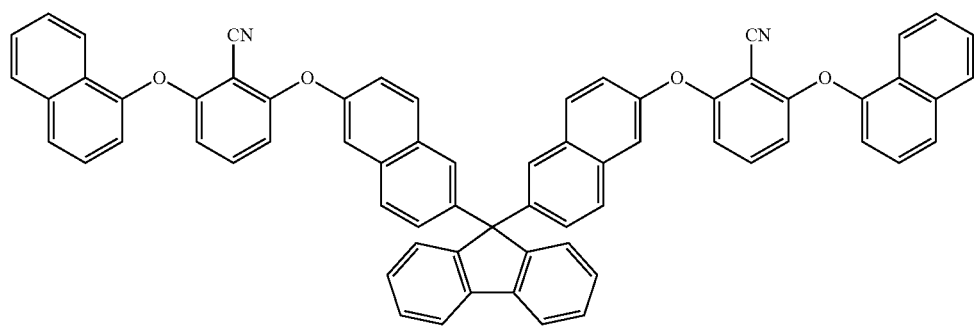

(A-15)

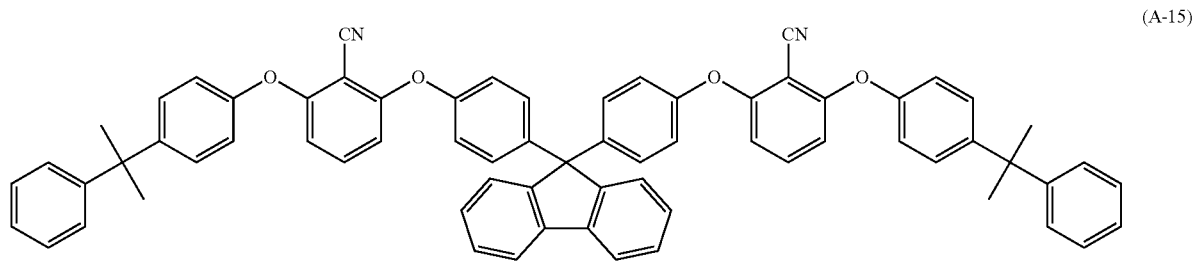

Comparative Synthesis Example 1

Synthesis of Polymer (A-1)

In a separable flask equipped with a thermometer, 140 parts by mass of the following compound (M-18), 100 parts by mass of the compound (M-19), 140 parts by mass of potassium carbonate as a basic compound and 500 parts by mass of dimethylacetamide as a solvent were blended under a nitrogen atmosphere, and then the condensation polymerization reaction was allowed to proceed at 140° C. for 4 hrs with stirring to obtain a reaction mixture. This reaction mixture was filtered, followed by addition of methanol thereto to permit reprecipitation, and the resulting precipitates were dried to obtain a polymer (a-1) having a structural unit represented by the following formula (a-1). The polymer (a-1) had an Mw of 4,000.

Comparative Synthesis Example 2

Synthesis of Compound (A-2)

Into a separable flask equipped with a thermometer were charged 100 parts by mass of 2,7-dihydroxynaphthalene, 30 parts by mass of formalin, 1 part by mass of p-toluenesulfonic acid and 150 parts by mass of propylene glycol monomethyl ether under a nitrogen atmosphere, and then the polymerization was allowed to proceed at 80° C. for 6 hrs with stirring to obtain a reaction mixture. The resulting reaction mixture was diluted with 100 parts by mass of n-butyl acetate, and the organic layer was washed with a large quantity of a mixed solvent of water and methanol (mass ratio: water/methanol=1/2). Thereafter, the solvent was distilled off to obtain a polymer (a-2) having a structural unit represented by the following formula (a-2). The polymer (a-2) had an Mw of 1,800.

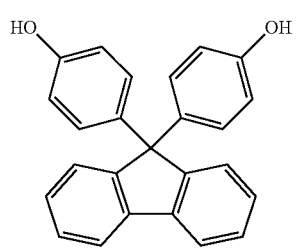

(M-18)

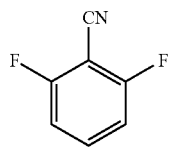

(M-19)

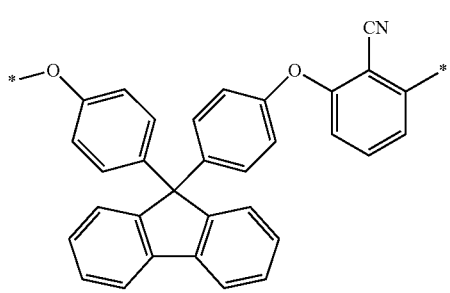

(a-1)

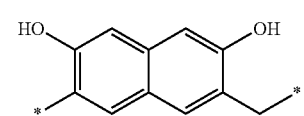

(a-2)

Preparation of Composition for Film Formation

Each component other than the component (A) is shown below.

(B) Solvent
 B-1: propylene glycol monomethyl ether acetate
 B-2: cyclohexanone (C) Acid Generating Agent
 C-1: bis(4-t-butylphenyl)iodonium nonafluoro-n-butanesulfonate (a compound represented by the following formula (C-1))

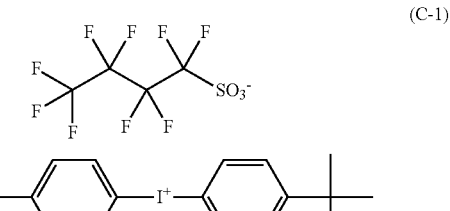

(C-1)

(D) Crosslinking Agent
 D-1: 4,4'-(1-(4-(1-(4-hydroxy-3,5-bis(methoxymethyl)phenyl)-1-methylethyl)phenyl)ethylidene)bis(2,6-bis(methoxymethyl)phenol) (a compound represented by the following formula (D-1))

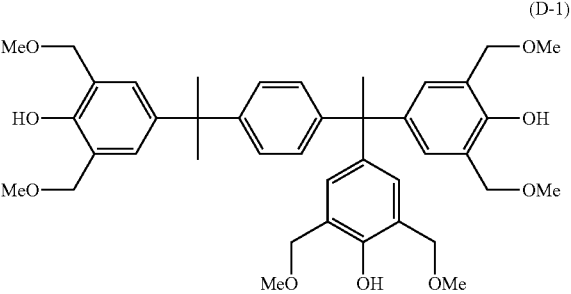 [SMILES: COCc1cc(C(C)(C)c2ccc(C(C)(c3cc(COC)c(O)c(COC)c3)c3cc(COC)c(O)c(COC)c3)cc2)cc(COC)c1O]

(D-1)

Example 16

A solution was obtained by mixing 10 parts by mass of (A-1) as the compound (A) and 100 parts by mass of (B-1) as the solvent (B). This solution was filtered through a membrane filter having a pore size of 0.1 μm to prepare a composition for film formation (J-1).

Examples 17 to 30 and Comparative Examples 1 and 2

Compositions for film formation (J-2) to (J-15), and (CJ-1) and (CJ-2) were prepared in a similar manner to Example 16 except that the type and the amount of each component were as specified in Table 1. It is to be noted that in Table 1, "-" indicates that the corresponding component was not used.

TABLE 1

| Composition for film formation | (A) Component type | amount (parts by mass) | (B) Solvent type | amount (parts by mass) | (C) Acid generating type | amount (parts by mass) | (D) Crosslinking type | amount (parts by mass) |
|---|---|---|---|---|---|---|---|---|
| Example 16 | J-1 | A-1 | 10 | B-1 | 100 | — | — | — | — |
| Example 17 | J-2 | A-2 | 10 | B-1 | 100 | — | — | — | — |
| Example 18 | J-3 | A-3 | 10 | B-1 | 100 | — | — | — | — |
| Example 19 | J-4 | A-4 | 10 | B-1 | 100 | — | — | — | — |
| Example 20 | J-5 | A-5 | 10 | B-1 | 100 | — | — | — | — |
| Example 21 | J-6 | A-6 | 10 | B-2 | 100 | — | — | — | — |
| Example 22 | J-7 | A-7 | 10 | B-1 | 100 | — | — | — | — |
| Example 23 | J-8 | A-8 | 10 | B-1 | 100 | — | — | — | — |
| Example 24 | J-9 | A-9 | 10 | B-1 | 100 | — | — | — | — |
| Example 25 | J-10 | A-10 | 10 | B-1 | 100 | — | — | — | — |
| Example 26 | J-11 | A-11 | 10 | B-1 | 100 | — | — | — | — |
| Example 27 | J-12 | A-12 | 10 | B-1 | 100 | — | — | — | — |
| Example 28 | J-13 | A-13 | 10 | B-1 | 100 | C-1 | 0.5 | D-1 | 1 |
| Example 29 | J-14 | A-14 | 10 | B-2 | 100 | C-1 | 0.5 | D-1 | 1 |
| Example 30 | J-15 | A-15 | 10 | B-1 | 100 | C-1 | 0.5 | D-1 | 1 |
| Comparative Example 1 | CJ-1 | a-1 | 10 | B-2 | 100 | — | — | — | — |
| Comparative Example 2 | CJ-2 | a-2 | 10 | B-2 | 100 | — | — | — | — |

Evaluations

Using the composition for film formation obtained as described above, evaluations were made in regard to etching resistance, heat resistance and flatness according to the following methods. The results of the evaluations are shown in Table 2.

Etching Resistance

The composition for film formation obtained as described above was spin-coated on a silicon wafer having a diameter of 8 inches to provide a film having a film thickness of 300 nm. Thereafter, the film was subjected to an etching treatment (pressure: 0.03 Torr; high frequency power: 3,000 W; Ar/CF$_4$=40/100 sccm; and substrate temperature: 20° C.), and the thickness of the film after the etching treatment was measured. The etching rate (nm/min) was calculated from the relationship between a decrease of the film thickness and the treatment time period, and the proportion of the etching rate of the film according to Examples with respect to that of the film according to Comparative Example 2 was calculated. The smaller value indicates more favorable etching resistance.

Heat Resistance

The composition for film formation obtained as described above was spin-coated on a silicon wafer having a diameter of 8 inches to provide a coating film, and the film thickness of the coating film was measured using the spectroscopic ellipsometer (the value of the film thickness acquired in this measurement being designated as X). Next, the film was heated at 350° C. for 120 sec, and the film thickness of the film after the heating was measured using the spectroscopic ellipsometer (the value of the film thickness acquired in this measurement being designated as Y). A percent decrease of the film thickness of the film after the heating with respect to the film thickness of the film before the heating (100×(X−Y)/X) (%) was calculated, and the value was defined as heat resistance. The smaller heat resistance indicates that the film is more favorable (i.e., more superior in heat resistance) as there are less sublimated matter and film degradation products generated during the heating of the film.

Flatness

The compositions for film formation obtained as described above was each applied on a SiO$_2$ stepped substrate on which: trenches having a width of 42 nm, a pitch of 84 nm and a depth of 180 nm (aspect ratio: 4.3); trenches having a width of 100 nm, a pitch of 150 nm and a depth of 180 nm (aspect ratio: 1.8); and trenches having a width of 5 μm and a depth of 180 nm (open spaces: aspect ratio: 0.036) were provided in combination, with the ratio of the maximum value to the minimum value in aspect ratios different from each other being 119). Thereafter, baking was carried out at 250° C. for 60 sec under an ambient air atmosphere to form a film having a film thickness of 200 nm. The shape of the film was observed using a scanning electron microscope ("S-4800" available from Hitachi High-Technologies Corporation), and the difference (ΔFT) of the maximum value and the minimum value of the thickness of the film on the trenches or spaces was determined. The flatness was evaluated to be "A" (favorable) in a case where the ΔFT was less than 20 nm, and to be "B" (unfavorable) in a case where the ΔFT was no less than 20 nm.

TABLE 2

| Composition for film formation | | Etching resistance | Heat resistance (%) | Flatness |
|---|---|---|---|---|
| Example 16 | J-1 | 0.93 | 10 | A |
| Example 17 | J-2 | 0.92 | 11 | A |
| Example 18 | J-3 | 0.94 | 12 | A |
| Example 19 | J-4 | 0.93 | 13 | A |
| Example 20 | J-5 | 0.93 | 13 | A |
| Example 21 | J-6 | 0.92 | 12 | A |
| Example 22 | J-7 | 0.93 | 11 | A |
| Example 23 | J-8 | 0.94 | 14 | A |
| Example 24 | J-9 | 0.94 | 11 | A |
| Example 25 | J-10 | 0.93 | 13 | A |
| Example 26 | J-11 | 0.94 | 12 | A |
| Example 27 | J-12 | 0.95 | 12 | A |
| Example 28 | J-13 | 0.94 | 13 | A |
| Example 29 | J-14 | 0.92 | 14 | A |
| Example 30 | J-15 | 0.94 | 14 | A |
| Comparative Example 1 | CJ-1 | 0.92 | 12 | B |
| Comparative Example 2 | CJ-2 | 1 | 20 | B |

As is clear from the results shown in Table 2, the films formed from the compositions for film formation of Examples satisfied general characteristics such as etching resistance, and exhibited superior heat resistance and superior flatness as compared with the films formed from the compositions for film formation of Comparative Examples.

INDUSTRIAL APPLICABILITY

The composition for film formation according to the present invention is capable of forming a film having superior heat resistance and flatness while general characteristics such as etching resistance are maintained. The film is superior in heat resistance and flatness. The method for producing a patterned substrate enables a resist underlayer film having superior heat resistance and flatness to be readily formed, and enables a favorable pattern to be formed on a substrate using the resist underlayer film having such superior characteristics. The compound can be suitably used as a component of the composition for film formation. Therefore, these can be suitably used in manufacture of semiconductor devices, and the like in which further progress of miniaturization is expected in the future.

What is claimed is:

1. A method for producing a patterned substrate, comprising:

applying a composition on an upper face side of a substrate to form a resist underlayer film;

forming a resist pattern directly or indirectly on the resist underlayer film; and etching using the resist pattern as a mask such that the substrate has a pattern, wherein the composition comprises:

a solvent; and a compound represented by formula (2):

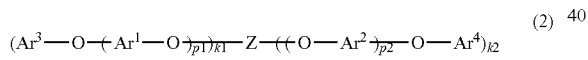

wherein, in the formula (2), Z represents a partial structure represented by formula (1); k1 and k2 are each independently an integer of 0 to 9, wherein a sum of k1 and k2 is no less than 1, and a sum of a1 and k1 and a sum of a2 and k2 are no greater than 9; $Ar^1$ and $Ar^2$ each independently represent a substituted or unsubstituted arenediyl group having 6 to 20 carbon atoms: $Ar^3$ and $Ar^4$ each independently represent a substituted or unsubstituted aryl group having 6 to 20 carbon atoms; and p1 and p2 are each independently an integer of 0 to 3, wherein in a case where $Ar^1$ to $Ar^4$, p1 and p2 are each present in a plurality of number, a plurality of $Ar^1$s may be identical or different, a plurality of $Ar^2$s may be identical or different, a plurality of $Ar^3$s may be identical or different, a plurality of $Ar^4$s may be identical or different, a plurality of p1s may be identical or different, and a plurality of p2s may be identical or different, and wherein a substituent present on the aryl group represented by $Ar^3$ and $Ar^4$ is an aralkyl group having 7 to 20 carbon atoms or a monovalent intermolecular bond-forming group having 1 to 20 carbon atoms which is a carbon-carbon double bond-containing group, a carbon-carbon triple bond-containing group, an acyl group or a combination thereof:

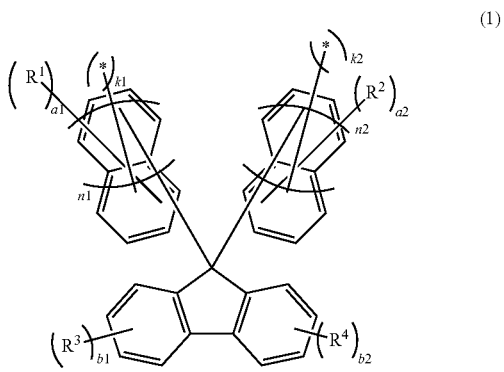

wherein, in the formula (1), $R^1$ to $R^4$ each independently represent a halogen atom, a hydroxy group, a nitro group or a monovalent organic group having 1 to 20 carbon atoms; a1 and a2 are each independently an integer of 0 to 9; b1 and b2 are each independently an integer of 0 to 4, wherein in a case where $R^1$ to $R^4$ are each present in a plurality of number, a plurality of $R^1$s may be identical or different, a plurality of $R^2$s may be identical or different, a plurality of $R^3$s may be identical or different, and a plurality of $R^4$s may be identical or different; n1 and n2 are each independently an integer of 0 to 2; k1 and k2 are as defined in the formula (2); and * denotes a binding site to the oxygen atom in the formula (2).

2. The method according to claim 1, wherein the carbon-carbon double bond-containing group is a group represented by formula (3-1), and the carbon-carbon triple bond-containing group is a group represented by formula (3-2),

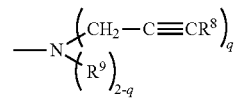

wherein, in the formula (3-1), $R^5$, $R^6$ and $R^7$ each independently represent a hydrogen atom or a monovalent hydrocarbon group having 1 to 20 carbon atoms, and wherein, in the formula (3-2), $R^8$ and $R^9$ each independently represent a hydrogen atom or a monovalent hydrocarbon group having 1 to 20 carbon atoms; and q is 1 or 2, wherein in a case where q is 2, a plurality of $R^8$s may be identical or different.

3. The method according to claim 1, wherein a molecular weight of the compound is no less than 300 and no greater than 3,000.

4. The method according to claim 1, wherein the solvent comprises a polyhydric alcohol partial ether acetate solvent, a ketone solvent, a carboxylic acid ester solvent or a combination thereof.

5. The method according to claim 1, wherein, in the formula (2), the aryl group represented by $Ar^3$, the aryl group represented by $Ar^4$, or both comprises a substituent.

6. The method according to claim 5, wherein the substituent present on the aryl group represented by $Ar^3$ or $Ar^4$ is the monovalent intermolecular bond-forming group.

7. The method according to claim 1, wherein, in the formula (1), a1 and a2 are each an integer of 0.

8. The method according to claim 7, wherein, in the formula (1), b1 and b2 are each an integer of 0.

9. The method according to claim 1 wherein, in the formula (2), p1 and p2 are each 1 or more, and $Ar^1$ and $Ar^2$ each represent a substituted or unsubstituted benzenediyl group.

10. The method according to claim 9, wherein, $Ar^1$ and $Ar^2$ each represent a substituted benzenediyl group.

11. The method according to claim 10, wherein, $Ar^1$ and $Ar^2$ each independently represent a benzenediyl group substituted with a nitro group or a cyano group.

12. The method according to claim 10, wherein, $Ar^1$ and $Ar^2$ each represent a benzenediyl group substituted with a cyano group.

13. The method according to claim 1, wherein, in the formula (1), n1 and n2 are each independently an integer of 0 or 1.

14. The method according to claim 1, wherein, in the formula (1), n1 and n2 are each an integer of 1.

15. The method according to claim 1, wherein, in the formula (1), n1 and n2 are each an integer of 0.

* * * * *